US010537610B1

(12) United States Patent
Babinska et al.

(10) Patent No.: US 10,537,610 B1
(45) Date of Patent: Jan. 21, 2020

(54) PEPTIDE FOR INHIBITION OF CANCER

(71) Applicants: Anna Babinska, Staten Island, NY (US); Radoslaw Bednarek, Lodz (PL); Elizabeth Kornecki, Cristiansted, VI (US); Moro O. Salifu, Brooklyn, NY (US); Yigal H. Ehrlich, Christiansted, VI (US); Maria Swiatkowska, Bedlno (PL); Cristina C. Clement, Bronx, NY (US)

(72) Inventors: Anna Babinska, Staten Island, NY (US); Radoslaw Bednarek, Lodz (PL); Elizabeth Kornecki, Cristiansted, VI (US); Moro O. Salifu, Brooklyn, NY (US); Yigal H. Ehrlich, Christiansted, VI (US); Maria Swiatkowska, Bedlno (PL); Cristina C. Clement, Bronx, NY (US)

( * ) Notice: Subject to any disclaimer, the term of this patent is extended or adjusted under 35 U.S.C. 154(b) by 0 days.

(21) Appl. No.: 16/169,118

(22) Filed: Oct. 24, 2018

(51) Int. Cl.
| | | |
|---|---|---|
| A61K 38/00 | (2006.01) |
| A61K 38/08 | (2019.01) |
| A61K 38/10 | (2006.01) |
| A61K 38/16 | (2006.01) |
| C07K 14/00 | (2006.01) |
| C07K 5/10 | (2006.01) |
| C07K 7/02 | (2006.01) |
| C07K 7/06 | (2006.01) |
| C07K 7/08 | (2006.01) |
| A61K 38/17 | (2006.01) |
| A61P 35/00 | (2006.01) |

(52) U.S. Cl.
CPC ............. *A61K 38/177* (2013.01); *A61P 35/00* (2018.01)

(58) Field of Classification Search
CPC ........ A61K 38/00; A61K 38/08; A61K 38/10; A61K 38/16; C07K 14/00; C07K 14/70503; C07K 5/10; C07K 7/02; C07K 7/06; C07K 7/08
USPC ........... 514/1.1, 19.4, 19.3, 21.6, 21.5, 21.4; 530/326, 327, 328, 329, 330
See application file for complete search history.

(56) References Cited

U.S. PATENT DOCUMENTS

| | | | |
|---|---|---|---|
| 5,744,460 A | 4/1998 | Muller et al. | |
| 7,829,663 B2 * | 11/2010 | Kornecki | ........... A61K 38/1709 424/185.1 |
| 8,557,957 B2 * | 10/2013 | Kornecki | ......... C07K 14/70503 424/185.1 |

OTHER PUBLICATIONS

International Search Report and Written Opinion dated Nov. 19, 2019 received in International Application No. PCT/US2019/057897.

* cited by examiner

*Primary Examiner* — Julie Ha
(74) *Attorney, Agent, or Firm* — Scully, Scott, Murphy & Presser, P.C.

(57) ABSTRACT

Methods for treating breast cancer, the methods can include administering to a subject an effective amount of a cell adhesion molecule Receptor (F11R peptide).

4 Claims, 6 Drawing Sheets

Specification includes a Sequence Listing.

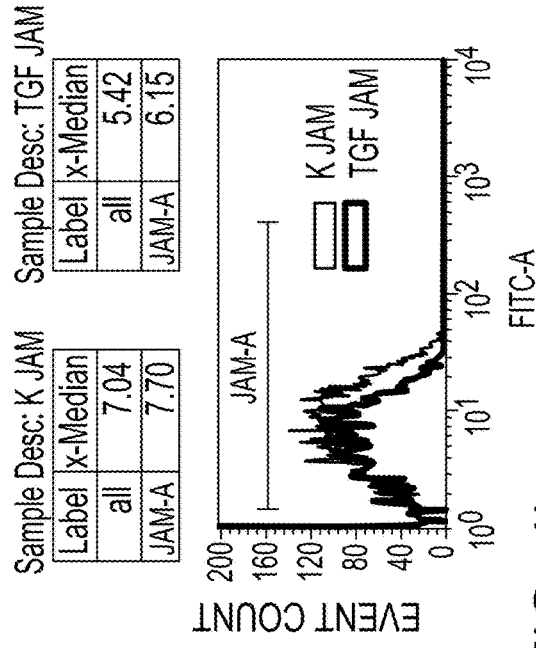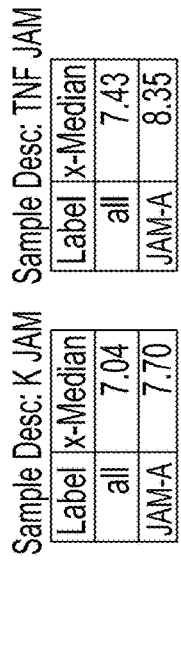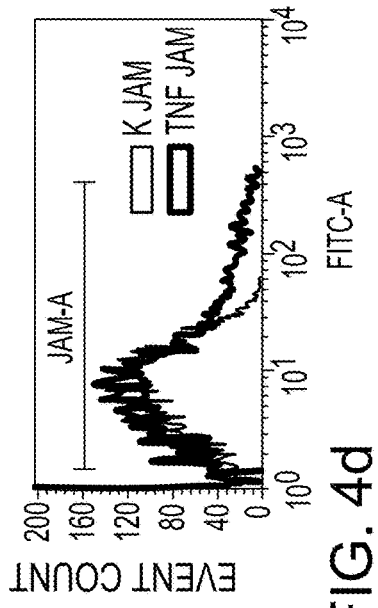
FIG. 4a
FIG. 4b
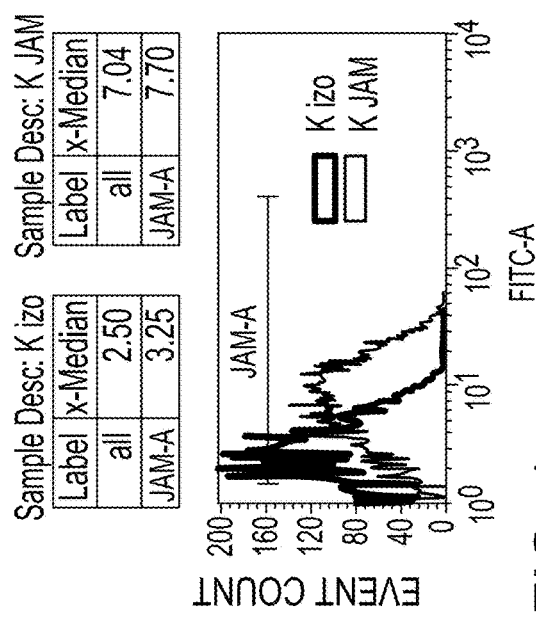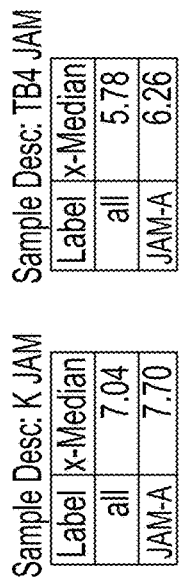
FIG. 4c
FIG. 4d

PEPTIDE FOR INHIBITION OF CANCER

INCORPORATION BY REFERENCE OF SEQUENCE LISTING

The Sequence Listing in the ASCII text file, named as 36167_SequenceListing.txt of 3 KB, created on Oct. 24, 2018, and submitted to the United States Patent and Trademark Office via EFS-Web, is incorporated herein by reference.

FIELD OF THE DISCLOSURE

The present disclosure relates to protein and peptide chemistry, as well as the treatment of cancer, including breast cancer. The present disclosure is directed to a cell adhesion molecule (CAM) and fragments thereof, and more particularly to a CAM designated as the F11 receptor (F11R), or a polypeptide fragment thereof.

BACKGROUND OF THE DISCLOSURE

Breast cancer is the most frequently diagnosed cancer and the leading cause of cancer death among females worldwide. Statistics provided by the International Agency for Research on Cancer an estimated 1.7 million cases and 521,900 deaths were recorded in 2012, thus accounting for 25% of all cancer cases and 15% of all cancer deaths among females. The incidence of the disease is generally higher in economically developed countries than in developing countries. Despite the progress in breast cancer care which has led to reduced mortality the incidence of the disease is continuously rising. In Poland the breast cancer mortality was over 3 times higher in the year 2013 than in 1980.

Regardless of the years of related research, the knowledge about breast cancer is still limited, particularly the molecular mechanism of metastasis is not completely understood. Breast cancer development, including metastasis, is a complex process comprising the interactions of cancer cells with the endothelium those involve a wide array of proteins. Therefore, it is of great importance to unravel the role of virtually each biologically active molecule in this pathological condition in order to obtain the complex vision of available targets for breast cancer treatment and thus to provide the ideas for the new strategies of anticancer therapy.

Embodiments of the present disclosure provide compounds and methods that address the above needs.

SUMMARY OF THE DISCLOSURE

The present disclosure is directed to methods for treating breast cancer, the methods can include administering to a subject an effective amount of a F11R peptide.

Nucleic acid molecules coding for any of the above F11R-antagonist proteins, fragments and peptides of the present disclosure, expression vectors which include any of such nucleic acid molecules, as well as related host cells containing such nucleotide sequences or vectors, are also contemplated by the present disclosure.

Still another embodiment of the present disclosure is directed to antibodies raised against the F11R-antagonist proteins, F11R antibody fragments, peptidomimetics and peptides of the present disclosure.

In accordance with the present disclosure, the F11R antagonists encompass compounds that mimic F11R, which when present in sufficient amounts will occupy one or more relevant molecular and/or cellular F11R binding sites that normally would be occupied by F11R in its role as a mediator of platelet aggregation and adhesion. These compounds include small molecule organic compounds, peptides, peptidomimetics, or polypeptides, that structurally resemble a portion of F11R and compete for F11R binding sites on homophilic or heterophilic F11R binding partners.

F11R antagonists also encompass compounds, peptides and polypeptides that bind directly to F11R thereby impairing its aggregative/adhesive function. This group encompasses small molecule organic compounds, ligands, polypeptides, antibodies or antibody fragments, recombinant engineered proteins and antibodies that specifically bind to a region on F11R thereby inhibiting its participation in platelet aggregation and adhesion.

In an even additional embodiment of the disclosure, the peptide or polypeptide may comprise the extracellular domain of F11R or an aggregation/adhesion inhibiting portion thereof. Non-limiting examples of such portions of the F11R extracellular domain are exemplified by SEQ ID NO: 1 or SEQ ID NO: 4. In general, more than one antagonist may be administered. This may be especially desirable when the administered antagonists have distinct modes of inhibition, such as: (a) one antagonist is from Group A and one is from Group B; (b) each of the administered antagonists is from Group A, but each mimics distinct portions of the F11R, and (c) each of the administered antagonists is from Group B, but each of the antagonist binds to a distinct portion of the F11R, thereby inhibiting the aggregating/adhesion functions of the respective portions of F11R.

With respect to embodiments encompassing antibody antagonists, the antibody or functional fragment thereof can be a chimeric antibody, a humanized antibody or an autoantibody. Non-limiting examples of such antibodies comprise M.Ab.F11, the Fab, Fab', or $F(ab')_2$.

Preferably, the antibodies of the present disclosure are raised against those F11R sequences and F11R-antagonist peptides whose sequences coincide with the corresponding sequences of a mammalian F11R or Junctional Adhesion Molecule (JAM) proteins. The antibodies of the present disclosure can recognize, antagonize or neutralize the activity of F11R. Both polyclonal antibodies and monoclonal antibodies of various chimeric combinations are contemplated by the present disclosure. Examples of such antibodies include M.Ab.F11.

These and other embodiments of the disclosure will be readily apparent to those of ordinary skill in view of the disclosure herein.

BRIEF DESCRIPTION OF THE FIGURES

The present disclosure will be better understood by reference to the following drawings, which are provided as illustrative of certain embodiments of the subject application, and not meant to limit the scope of the present disclosure.

FIGS. 4a-4d are illustrations of flow cytometry analysis of JAM-A (CD321) expression on the surface of HMEC-1 cells. The cells were untreated (Control, K, black color) or treated with 200 nM of thymosin β4 (4(c)TB4, red color), 10 ng/ml of TGF-β1 (4(b) TGF, green color) or 10 ng/ml of TNF-α (4(d) TNF, blue color) for 24 hours. For the superficial visualization of JAM-A antigen, the cells were labeled with FITC anti-human CD321 Mouse IgG$_1$ Antibody (JAM) or with the corresponding isotype control (4(a) izo, purple color). The representative results of 3 independent experiments are shown.

FIG. 7 is a number of TEM images of breast cancer cells. Microscopic photographs presenting the fluorescently labeled breast cancer cells (MCF-7, MDA-MB-231) or non-tumorigenic MECs (MCF-10A) those transmigrated across the endothelial monolayer. The corresponding plots and detailed specifications are shown in FIG. 5b.

DETAILED DESCRIPTION OF THE DISCLOSURE

Figure 1B:
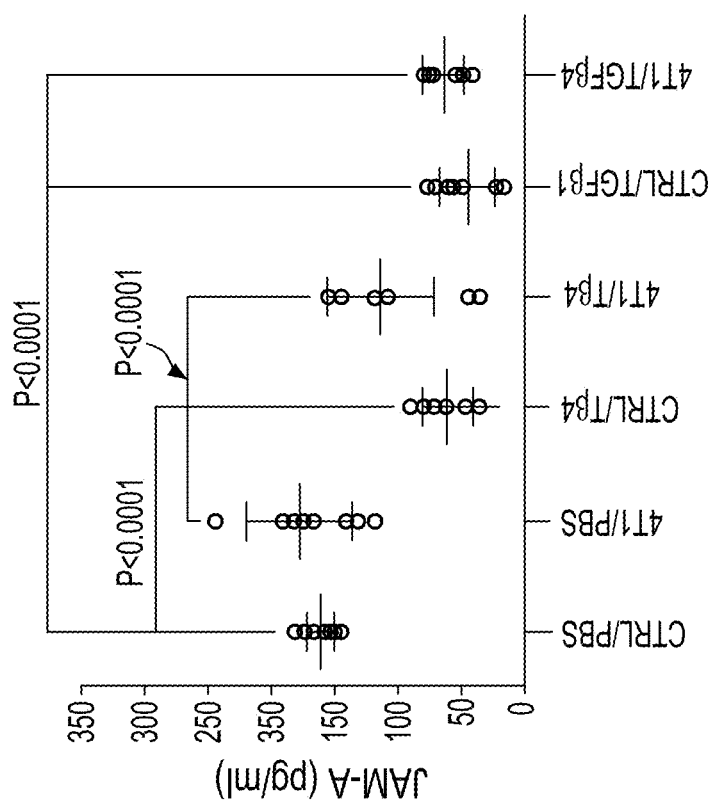
FIGS. 1a and 1b are illustrations of levels of Tβ4 (a) and JAM-A (b) antigens measured by ELISA in plasma from mice with (4T1) or without (CTRL) breast cancer induction and treated with Tβ4, TGF-β1 or vehicle (PBS) as described in Material and Methods section. Results are expressed as arithmetic means±SD (n=10). Statistical analysis was performed by one-way ANOVA with Tukey's multiple comparison post-hoc test.

In the discussion and claims herein, the term "about" indicates that the value listed may be somewhat altered, as long as the alteration does not result in nonconformance of the process or device. For example, for some elements the term "about" can refer to a variation of ±0.1%, for other elements, the term "about" can refer to a variation of ±1% or ±10%, or any point therein.

As used herein, the term "substantially", or "substantial", is equally applicable when used in a negative connotation to refer to the complete or near complete lack of an action, characteristic, property, state, structure, item, or result. For example, a surface that is "substantially" flat would either completely flat, or so nearly flat that the effect would be the same as if it were completely flat.

As used herein terms such as "a", "an" and "the" are not intended to refer to only a singular entity, but include the general class of which a specific example may be used for illustration.

As used herein, terms defined in the singular are intended to include those terms defined in the plural and vice versa.

References in the specification to "one embodiment", "certain embodiments", some embodiments" or "an embodiment", indicate that the embodiment(s) described may include a particular feature or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. For purposes of the description hereinafter, the terms "upper", "lower", "right", "left", "vertical", "horizontal", "top", "bottom", and derivatives thereof shall relate to the invention, as it is oriented in the drawing figures. The terms "overlying", "atop", "positioned on" or "positioned atop" means that a first element, is present on a second element, wherein intervening elements interface between the first element and the second element. The term "direct contact" or "attached to" means that a first element, and a second element, are connected without any intermediary element at the interface of the two elements.

Reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc.

The present disclosure is directed to F11R-antagonists and particularly antibody directed against F11R, the Fab, Fab', F(ab')$_2$ fragments of such antibody, as well as single-chain anti-F11R antibodies. By "F11R-antagonist" is meant molecules that inhibit, suppress or cause the cessation of at least one F11R-mediated biological activity by, e.g., interfering with, blocking or otherwise preventing or regulating the interaction or binding of F11R to its target, e.g. F11R on another cell, or another protein that F11R binds to such as itself or other JAMs, to the leukocyte function associated antigen-1 (LFA-1)(Ostermann et al., 2002, Nat. Immunol. 3, 151-158), the integrins GPIIb/IIIa and $\alpha_v\beta_3$, as well as other binding proteins.

In accordance with the present disclosure, F11R-antagonist peptides derived from or corresponding to the F11R have been isolated and synthesized. These peptides possess F11R antagonistic properties including the ability to selectively bind to F11R and inhibit F11R-mediated biological activity which, for example, is associated with adhesion of platelets to endothelial cells in mammals. The peptides of the present disclosure preferably correspond to specific portions of the native human F11 receptor and include variations thereof, and therefore are non-immunogenic when administered to humans. The peptides of the present disclosure can effectively block collagen-induced platelet aggregation and secretion and thereby are efficacious in regard to, inter alia, the prevention of excessive bleeding following an injury, under physiological conditions. Moreover, under pathological conditions, the uncontrolled accumulation of platelets in the vasculature, on the luminal surface of the inflamed endothelium or at exposed collagen sites within the injured vasculature results in excessive platelet aggregation, plaque and thrombus formation, atherosclerosis and stroke. In the context of the disclosure, the term "subject in need thereof" can be an animal, mammal or human that is at risk for, or is already experiencing symptoms of the foregoing conditions. The collagen-induced platelet aggregation blocking ability of the F11R-antagonist peptides of the present disclosure provides heretofore unrecognized treatment and prevention options in subjects in need thereof, i.e., diseases and disorders associated with excessive platelet aggregation.

The F11R-antagonist peptides of the present disclosure substantially correspond to the amino acids of the N-terminus or first Ig domain of human F11R.

A preferred F11R-antagonist peptide of the present disclosure is a sequence of the N-terminal peptide of the F11R structure: SVTVHSSEPEVRIPENNPVKLSC (SEQ ID NO: 1).

Another preferred F11R-antagonist peptide of the present disclosure is a sequence within the first Ig fold of the F11R structure: KSVTREDTGTYTC (SEQ ID NO: 4).

As used herein, "P4D" or "peptide 4D" refers to the 97-109 amino acid fragment of the nascent protein. P4D is a D-amino acid analog of the native peptide, designed for enhanced stability in in vivo environment that is abundant in proteases. The sequence of Scrambled P4D peptide (Scr) corresponded to P4D peptide, but was scrambled by random insertion of amino acid residues during the synthesis process. Therefore, the sequences of the JAM-A derived peptides used in this disclosure are as follows: NH$_2$-(dK)-SVT-(dR)-EDTGTYTC-CONH$_2$ (SEQ ID NO: 2) for P4D and NH$_2$—S-(dK)-TVE-(dR)-TDTGTYC-OH (SEQ ID NO: 3) for Scr.

The present disclosure is also directed to homologs, analogs and fragments of these peptides which maintain F11R-antagonist activity in a mammal, particularly humans are also contemplated by the present disclosure.

The term "compound" is taken to include both organic compounds such as peptides, as well as inorganic compounds such as ion chelators or opiates. Antibodies, e.g., polyclonal or monoclonal antibodies directed against F11R, the Fab, Fab', F(ab')$_2$ fragments of such antibodies, as well as single-chain anti-F11R antibodies can also be considered as compounds useful in the present methods.

When applicable, an anti-F11R antibody (e.g., M.Ab.F11) or antigen-binding fragment thereof is a humanized antibody. A "humanized antibody" is an antibody in which protein engineering is used to reduce the amount of 'foreign' protein sequence by substituting host antibody (e.g., mouse, rat) constant regions and the variable-domain framework regions with sequences that are found in human antibodies. It is further contemplated that when complete antibody molecules are to be employed, they may also be humanized or chimeric antibodies. Generally, a "chimeric antibody" is one where the constant regions of host origin, e.g., mouse or rat, are replaced by those of a human antibody.

Other compounds include chemical compounds that can be derived from the knowledge of the sequence of the F11R, from each of the above sequences and from the combination of the sequences together. These include linear sequences, cyclic sequences, annealing of the peptides together (including SEQ ID NOS: 1 and 4), and any other possible derivations using standard peptide chemistry techniques. In one embodiment the present disclosure contemplates any compound whose structure is based on the interaction of peptides 1 and 4 (SEQ ID NOS. 1 and 4), which form the binding site of the mature human platelet F11R.

Modifications to a specific peptide may be deliberate, as through site-directed mutagenesis and amino acid substitution during biosynthesis, or may be accidental such as through mutations in hosts, which produce the peptide. Peptides including derivatives can be obtained using standard mutagenesis techniques such as those described in Sambrook et al., Molecular Cloning, Cold Spring Harbor Laboratory Press (1989). For example, Chapter 15 of Sambrook describes procedures for site-directed mutagenesis of cloned DNA. Derivatives of SEQ ID NOs.: 1 and 4 include, but are not limited by modification occurring during or after translation, for example, by phosphorylation, glycosylation, crosslinking, acylation, proteolytic cleavage, linkage to a therapeutic protein, an antibody molecule, membrane molecule or other ligand (see Ferguson et al., 1988, *Annu. Rev. Biochem.* 57:285-320). Specific types of genetically produced derivatives also include, but not limited by amino acid alterations such as deletions, substitutions, additions, and amino acid modifications. A "deletion" refers to the absence of one or more amino acid residue(s) in the related peptide. An "addition" refers to the presence of one or more amino acid residue(s) in the related peptide. Additions and deletions to a peptide may be at the amino terminus, the carboxy terminus, and/or internal, can be produced by mutation in e.g., SEQ ID NO: 1 encoding DNA and/or by peptide post-translation modification. Amino acid "modification" refers to the alteration of a naturally occurring amino acid to produce a non-naturally occurring amino acid. Analogs of e.g. SEQ ID NO: 1 with unnatural amino acids can be created by site-specific incorporation of unnatural amino acids into polypeptides during the biosynthesis, as described in Christopher J. Noren, Spencer J. Anthony-Cahill, Michael C. Griffith, Peter G. Schultz, 1989 *Science*, 244: 182-188. A "substitution" refers to the replacement of one or more amino acid residue(s) by another amino acid residue(s) in the peptide. Mutations can be made in e.g., SEQ ID NO: 1 encoding DNA such that a particular codon is changed to a codon, which codes for a different amino acid. Such a mutation is generally made by making the fewest nucleotide changes possible. A substitution mutation of this sort can be made to change an amino acid in the resulting peptide in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting peptide. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids. Although proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp). Derivatives can contain different combinations of alterations including more than one alteration and different types of alterations.

The ability of the derivative to retain some activity can be measured using techniques described herein and/or using techniques known to those skilled in the art for measuring the F11R receptor binding activity. "Derivatives" of e.g., SEQ. ID. NO.: 1 are functional equivalents having similar amino acid sequence and retaining, to some extent, the activities of SEQ ID NO: 1. By "functional equivalent" is meant the derivative has an activity that can be substituted for the activity of SEQ. ID NO: 1. Preferred functional equivalents retain the full level of F11R-binding activity as measured by assays known to these skilled in the art. Preferred functional equivalents have activities that are within 1% to 10,000% of the activity of e.g., SEQ ID NO: 1, more preferably between 100% to 1000%, and more preferably within 50% to 200%. Derivatives have at least 50% sequence similarity, preferably 70%, more preferably 90%, and even more preferably 95% sequence similarity to SEQ. ID. NO: 1. "Sequence similarity" refers to "homology" observed between amino acid sequences in two different polypeptides, irrespective of polypeptide origin. A "residue" refers to an amino acid incorporated in the peptide by an amide bond, for example.

"F11R" refers to a receptor protein on the surface of human platelets as a target for a stimulatory M.Ab.F11.

"F11R" is also referred to as human ortholog of the murine protein called junctional adhesion molecule (JAM), specifically named JAM-1 and JAM-A. F11R from either platelets or endothelial cells comprises an extracellular domain consisting of two Ig-folds, a transmembrane domain and a short cytoplasmic portion. The cDNA encoding the F11R can be engineered, e.g., to delete the transmembrane and cytoplasmic domain thereby providing a polynucleotide encoding the extracellular domain. Expression of the F11R extracellular domain in eukaryotic cells results in its synthesis and secretion, thereby indicating that it is a soluble polypeptide.

Figure 1A:
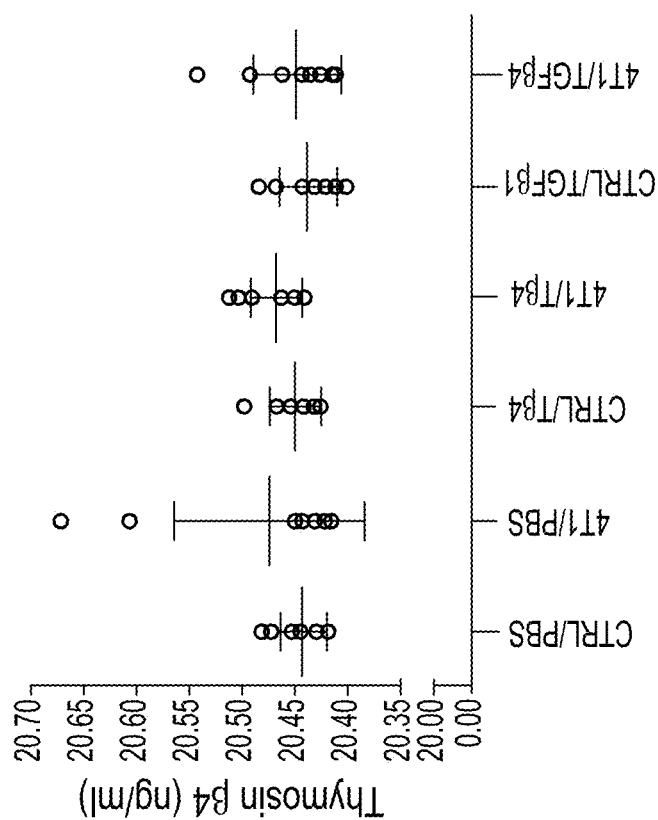

"F11R antagonists" and "F11R antagonist peptides" further refers to any compound that can bind to the active site of the F11R protein, specifically, but not limited to a pocket formed by the N-terminal 23 amino acid region and 13 amino acid region in the first Ig fold. By such binding, the action of F11R is inhibited, i.e. alignment of platelets and endothelial cells in F11R-mediated trans-homophilic interaction through the steric pocket, as depicted in FIGS. 1(a)-1(b), is blocked so that platelet aggregation or thrombosis, atherosclerosis, heart attacks, strokes, and all other human disorders that involve thrombus formation, can be prevented or treated. By "F11R antagonist peptide" is also meant a peptide that inhibits, suppresses or causes the cessation of at least one F11R mediated biological activity by e.g. interfering with or otherwise preventing the interaction or binding of platelets to endothelial cells and thereby inhibit platelet aggregation or interfering with the role of some protein in angiogenesis and thus preventing the growth of tumors.

As used herein, "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present disclosure. According to the present disclosure, preferred F11R antagonists include peptides (referred to herein as "F11R antagonist peptides") and antibodies. Additionally, analogs, homologs and fragments of the novel peptides provided herein are included within the scope of the term "F11R antagonist peptide".

By "homologs" is meant the corresponding peptides from F11R proteins of other mammalian species substantially homologous at the overall protein (i.e., mature protein) level to human F11R, so long as such homologous peptides retain the F11R antagonist activity.

By "analogs" or "F11R-Antagonist Peptide Analysis" is meant peptides which differ by one or more amino acid alterations, which alterations, e.g., substitutions, additions or deletions of amino acid residues, do not abolish the F11R antagonist properties of the relevant peptides. Thus, an analog can comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another. Likewise, the present disclosure contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cyteine, glutamine, glutamic acid, lysine and/or a polar residue for a non-polar residue.

The phrase "conservative substitution" also includes the use of chemically derivatized residues in place of a non-derivatized residues as long as the peptide retains the requisite F11R antagonist, inhibition properties as conventionally measured. Analogs also include the presence of additional amino acids or the deletion of one or more amino acids which do not affect F11R-mediated biological activity. For example, analogs of the subject peptides can contain an N- or C-terminal cysteine, by which, if desired, the peptide can be covalently attached to a carrier protein, e.g., albumin. Such attachment, it is believed, will minimize clearing of the peptide from the blood and also prevent proteolysis of the peptides. In addition, for purposes of the present disclosure, peptides containing D-amino acids in place of L-amino acids are also included in the term "conservative substitution". The presence of such D-isomers can help minimize proteolytic activity and clearing of the peptide.

The term "fragment" refers to any subject peptide having an amino acid sequence shorter than that of any peptide depicted in the submitted sequence listing and which fragment retains the F11R-mediated antagonist activity of the subject peptides.

The practice of the present disclosure employs, unless otherwise indicated, conventional techniques of synthetic organic chemistry, protein chemistry, molecular biology, microbiology, and recombinant DNA technology, which are well within the skill of the art. These techniques are applied in connection with peptide synthesis, recombinant production of peptides and peptide mutagenesis, for example. Such techniques are explained fully in the literature. See e.g., Scopes, R. K., *Protein Purification Principles and Practices*, 2d ed. (Springer-Verlag. 1987), *Methods in Enzymology* (M. Deutscher, ed., Academic Press, Inc. 1990), Sambrook, et al., *Molecular Cloning: A laboratory Manual*, 2d ed., (Cold Spring Harbor Press, Cold Spring Harbor, N.Y., 1989), *Handbook of Experimental Immunology*, Vols. I-IV (D. M. Weir and C. C. Blackwell, eds., 1986, Blackwell Scientific Publications), House, *Modern Synthetic Reactions,* 2d ed., (Benjamin/Cummings, Menlo Park, Calif., 1972).

The peptides of the present disclosure, homologs, analogs and fragments thereof can be synthesized by a number of known techniques. For example, the peptides may be prepared using the solid-phase synthetic technique initially described by Merrifield, in J. Am. Chem. Soc. 85:2149-2154 (1963). Other peptide synthesis techniques can be found in M. Bodanszky, et al. *Peptide Synthesis*, John Wiley & Sons, 2d Ed., (1976) and other references readily available to those skilled in the art. A summary of polypeptide synthesis techniques can be found in J. Stuart and J. D. Young, *Solid Phase Peptide Synthesis*, Pierce Chemical Company, Rockford, Ill., (1984). Peptides may also be synthesized by solution methods as described in *The Proteins*, Vol. II. 3d Ed., Neurath, H. et al., Eds., p. 105-237, Academic Press, New York, N.Y. (1976). Appropriate protective groups for use in different peptide syntheses are described in the above-mentioned texts as well as in J. F. W. McOmie, *Protective Groups in Organic Chemistry*, Plenum Press, New York, N.Y. (1973). The peptides of the present disclosure can also be prepared by chemical or enzymatic cleavage from larger portions of the F11R molecule or from the entire F11R molecule.

Additionally, the peptides of the present disclosure can also be prepared by recombinant DNA techniques (see e.g. *Current Protocols in Molecular Cloning* Ausubel et al., 1995, John Wiley & Sons, New York); Sambrook et al., 1989, *Molecular Cloning: A Laboratory Manual*, Second Edition, Cold Spring Harbor Laboratory Press, New York; Coligan et al. *Current Protocols in Immunology*, John Wiley & Sons Inc., New York, N.Y. (1994)). The skilled artisan understands that any of a wide variety of expression systems can be used to provide the recombinant peptides of the present disclosure. The precise host cell used is not critical to the disclosure. The F11R antagonist peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection. Manassas, Va. The method of transfection and the choice of expression vehicle will depend on the host system selected. Transformation and transfection methods are described, e.g. in Sambrook et al. supra; expression vehicles can be chosen from those provided e.g. in *Cloning Vectors: A Laboratory Manual* P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject F11R antagonist peptide. The present disclosure also contemplates a deoxyribonucleic acid (DNA) molecule or segment that defines a gene coding for, i.e., capable of expressing, a subject peptide or a subject chimeric peptide from which a peptide of the present disclosure can be enzymatically or chemically cleaved.

DNA molecules that encode peptides of the present disclosure can be synthesized by chemical techniques, for example, the phosphotriester method of Matteuccie, et al., *J. Am. Chem. Soc.* 103:3185 (1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present disclosure are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

In another embodiment of the present disclosure, one or more F11R antagonists, e.g., F11R antagonist peptides, peptidomimetics or antibodies, are included in pharmaceutical compositions.

Preferably, compositions containing the F11R antagonist peptides or peptidomimetics of the present disclosure are administered intravenously to inhibit, suppress, or cause the cessation of at least one F11R-mediated biological activity. When administered intravenously, the peptide compositions can be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present disclosure include, but are not limited to anti-F11R antibodies, NSAIDS, steroids, or cyclosporin-A. When employed together with F11R antagonists, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride can be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary. Further to administration by injection intravenously, peptides may also be administered parenterally intramuscularly, intraperitoneally, intrathecally, in a suppository, transdermally, topically, or orally.

When the peptides or peptidomimetics of the disclosure are administered orally, the pharmaceutical compositions thereof containing an effective dose of the peptide can also contain an inert diluent, as assimilable edible carrier and the like, be in hard or soft shell gelatin capsules, be compressed into tablets, or can be in an elixir, suspension, syrup or the like.

The subject peptides or peptidomimetics are thus compounded for convenient and effective administration in pharmaceutically effective amounts with a suitable pharmaceutically acceptable carrier in a therapeutically effective dose.

The peptides and peptidomimetics should preferably be administered in an amount of at least about 50 mg per dose, more preferably in an amount up to about 500 mg to about 1 gram per dose. Since the peptide compositions of this disclosure will eventually be cleared from the bloodstream, re-administration of the compositions is indicated and preferred.

The peptides and peptidomimetics can be administered in a manner compatible with the dosage formulation and in such amount as well be therapeutically effective. Systemic dosages depend on the age, weight and conditions of the patient and on the administration route. For example, a suitable dose for the administration to adult humans ranges from about 1 mg/kg of body weight about 10 mg per kilogram of body weight. The present disclosure also contemplates that the peptide or peptidomimetic compositions can be suitably coated on stents, lines, and tubes with a therapeutically effective amount of the peptide which amount can be readily determined by the skilled practitioner.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present disclosure vary according to the mode of administration. For example, the compositions can be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like can be used. In addition, carriers such as liposomes and microemulsions can be used.

In a further aspect of the present disclosure, the pharmaceutical compositions of the present disclosure are employed for the treatment various cancers, including breast cancer. Thus, the present disclosure provides methods of treating a disease in a subject by administering a therapeutically effective amount of a pharmaceutical composition of the present disclosure.

The term "therapeutically effective amount" means the dose required to treat a disease.

The term "treatment" or "treat" refers to effective inhibition, suppression or cessation of the F11R activity so as to prevent or delay the onset, retard the progression or ameliorate the symptoms of the disorder.

The term "subject" refers to any mammalian subject. Preferably, the subject is a human.

The F11R antagonist peptides of the present disclosure (or homologs, analogs or fragments) can be used to raise single-chain antibodies (SAb) or humanized monoclonal antibodies useful in the disclosure. The peptides can be coupled to a carrier protein such as KLH as described in Ausubel et al. (1989) *Current Protocols in Molecular Biology*, John Wiley & Sons, New York. The KLH-antagonist peptide is mixed with Freund's adjuvant and injected into guinea pigs, rats, donkeys and the like or preferably into rabbits. Antibodies can be purified by peptide antigen affinity chromatography.

The disclosure is further illustrated by the following specific examples which are not intended in any way to limit the scope of the disclosure.

In the following examples, there is a focus on a cell adhesion molecule (CAM) that is known under its official name as junctional adhesion molecule-A (JAM-A). The human JAM-A protein is found in UniProt Knowledge Base (UniProtKB) under the entry name JAM1_HUMAN (UniProtKB AC: Q9Y624). In the published papers JAM-A is also designated as JAM-1, CD321 or F11 receptor (F11R). JAM-A is expressed on the surface of human platelets and at the TJs of vascular endothelial and epithelial cells where homophilic interactions between JAM-A molecules are formed. This protein is known to play a role in inflammatory thrombosis, hypertension and brain ischemia. JAM-A was identified in the enriched hematopoietic stem cell fraction as well as in the atherosclerotic plaques of coronary artery disease patients. The expression level of JAM-A positively correlates with inflammatory cytokines including tumor necrosis factor-α, interleukin-δ, interleukin-10, and interferon-γ.

The inflammatory markers are important constituents of tumor microenvironment and inflammation plays a prominent role in breast cancer progression. Inflammatory conditions induce disappearance of JAM-A from intercellular junctions and subsequent redistribution toward the apical regions of endothelial cells. Consequently, JAM-A molecules are localized onto luminal surfaces of the endothelium and are able to interact with integrins and other proteins on leukocyte surfaces, thus promoting transendothelial migration (TEM) of leukocytes. Moreover, translocation of JAM from TJ to luminal endothelial surface leads to increased permeability of blood vessels thus facilitating TEM. Cancer cells contribute to TEM in a roughly similar way to leukocytes. JAM-A was shown to promote TEM of monocytes in breast cancer as well as to inhibit TEM of melanoma cells but its effect on extravasation of breast cancer cells is not fully investigated.

Aberrant expression of JAM-A has been shown to be characteristic for tumor progression. However, the effect of JAM-A on tumor development is complex and the role of JAM-A in tumor progression may be regulated in a tissue-dependent manner. The prominent role of JAM-A in breast cancer is manifested by the pleiotropic action of JAM-A in regulating both the mammary gland epithelium and the cells of microenvironment, including endothelium. Nevertheless, the specific contribution of JAM-A to breast cancer progression remains controversial. Knockdown of JAM-A has been shown to enhance invasiveness of the breast cancer cell lines MDA-MB-231 and T47D, whereas the overexpression of JAM-A inhibited both migration and invasion of MDA-MB-231 cells through collagen gels, suggesting that loss of JAM-A expression increases cancer cell dissemination and invasion.

There is a significant association between high JAM-A expression and poor survival in two large cohorts of patients with invasive breast cancer, and simultaneously a decrease of migration of high JAM-A expressing MCF-7 breast cancer cells upon knockdown or functional inhibition of JAM-A. The reduced cell motility after JAM-A downregulation could be a result of diminished association between the cytoplasmic tail of JAM-A and the PDZ-GEF2 protein that consequently reduced the activation of Rap1, a member of the Ras family of small GTPases and a potent regulator of β1-integrins and of breast tumorigenesis. This was supported by two studies: the first one showing that overexpression of another microRNA, namely miR-145, in breast cancer cells led to a decrease in cellular migration and invasion via downregulation of JAM-A expression and the second one providing the histopathological evidence that JAM-A overexpression is a poor prognostic factor in breast cancer patients due to the fact that JAM-A protects tumor cells from apoptosis.

Thymosin β4 (Tβ4), a small, ubiquitous 43-amino acid protein, is the most abundant member of the β-thymosins, a family of highly conserved polar 5-kDa peptides. The native actin-binding peptide is found in high concentrations in the majority of tissue types, with the highest concentrations in blood platelets and white blood cells. Tβ4 is also detected outside the cells in blood plasma or in wound fluid. Moreover, Tβ4 accelerates angiogenesis and wound healing, cell survival and cardiac repair, reduces inflammatory response and stimulates tumor metastasis by activating cell migration and angiogenesis. Tβ4-based drug candidates are currently the subject of late stage clinical trials in the USA, China and Korea for patients with dry eye syndrome, pressure and venous stasis ulceration, epidermolysis bullosa and neurotrophic keratopathy.

It has been demonstrated that the chemotherapeutic drug tamoxifen decreased the level of Tβ4 in MCF-7 breast cancer cell line and changed F-actin staining from a fuzzy morphology to a quite well-defined lining at the sites of cell-cell contact, suggesting a restriction in cell surface dynamics. Simultaneously, elevated expression of Tβ4 was found in several breast cancer cell lines as compared with a non-tumorigenic mammary epithelial cell (MEC) line MCF-12A. Results of another study showed a diffuse cytoplasmic and pronounced nuclear localization of the peptide in MCF-7 cells and it was suggested, that Tβ4 was specifically translocated into the cell nucleus by an active transport mechanism, requiring an unidentified soluble cytoplasmic factor. The study on distribution of the peptide in invasive breast cancer tissues revealed that Tβ4 showed low or intermediate immunofluorescence signal in cancer cells, whereas the intense reactivity was found in the cells of tumor microenvironment, including endothelium.

Moreover, in breast ductal infiltrating carcinomas a strong reactivity for Tβ4 was evident in tumor infiltrating and peritumoral mast cells. Finally, it has been demonstrated that Tβ4 expression significantly correlated with lymph node metastasis in breast carcinoma and was highly associated with the expression of hypoxia inducible factors HIF-1α and HIF-2α. It was determined that Tβ4 is induced by hypoxia, which then regulates HIF-α expression and increases production of vascular endothelial growth factor. Furthermore, Tβ4 overexpression was significantly correlated with lymph node metastatic potential of breast cancer.

The following examples are directed to the molecular mechanisms that explain the interactions between the breast cancer cells and endothelial cells of tumor microenvironment those lead to breast cancer development and metastasis. In particular, the role of JAM-A in breast cancer cells and endothelial cells activated with Tβ4 was reviewed. In these examples a mouse 4T1 breast cancer model was relied on and was used to perform a series of experiments with Tβ4-activated breast cancer cells and endothelial cells. Subsequently, the obtained results were compared with the cytokine-activated cells, and the cells treated with the F11R P4D peptide that blocks the homophilic interactions between the JAM-A molecules, thus inhibiting tight junctions (TJ) formation. The amounts of the soluble JAM-A (sJAM-A) in the blood plasma obtained from 4T1 tumor-bearing mice were measured by ELISA. The levels of JAM-A mRNA and protein in cell lines were assessed by qRT-PCR and Western blot, respectively. Cell surface expression of JAM-A was demonstrated by flow cytometry.

Transmigration of breast cancer cells across the endothelial monolayer was performed in Transwell devices, whereas adhesion of breast cancer cells to endothelial monolayer was assayed under static conditions. The permeability of endothelial monolayer was analyzed by the macromolecular permeability assay with the use of Transwell inserts and FITC-dextran as a tracer as well as by the non-invasive impedance monitoring with the RTCA instrument. Higher expression level of JAM-A protein was observed in cancer cells as compared to non-cancerous cells, but this effect was ambiguous in the case of breast cancer cell lines. Moreover, exogenously added Tβ4 significantly reduced the protein level of JAM-A in human microvascular endothelial cell line HMEC-1. Furthermore, F11R P4D peptide inhibited the interactions between breast cancer cells and cytokine-inflamed endothelium (adhesion, transendothelial migration). The following examples on endothelial permeability using the fluorescent macromolecular tracer provided the evidence that P4D abrogated de novo formation of TJ without breaking the preexisting ones, thus it hindered the interactions between breast cancer cells and endothelial cells without the simultaneous disruption of endothelial monolayer.

Also, the real-time impedance-based analysis of endothelial permeability revealed, that the barrier-protecting effect of P4D was even more evident than that forskolin, when endothelial monolayer was treated with P4D twice: shortly (ca. 2.5 hours) after seeding, and ca. 60 hours later simultaneously with the proinflammatory cytokines (TNFα and IFNγ). The obtained data explain the significance of JAM-A protein activity in Tβ4-activated breast cancer development.

Further, the following examples demonstrate the role of JAM-A in the transmigration of breast tumor cells across inflamed endothelium. It is shown that that several tumor inducers, including Tβ4 and TGF-β1 can decrease the plasma levels of sJAM-A. This in turn increases the interactions between the cancer cells and endothelium thus leading to tumor metastasis. Decreased level of sJAM-A can be restored by JAM-A derived peptide P4D, which blocks the extravasation of breast cancer cells in two steps: (1) adhesion and (2) transendothelial migration. Moreover, P4D is shown to abrogate the adhesion of breast cancer cells to the inflamed endothelium as well as the cytokine-induced TEM of breast cancer cells. Thus, P4D peptide can be considered for administration to prevent breast cancer metastasis.

Example 1

This example was focused on the significance of inflammatory response in breast cancer progression. There was a particular interest in the role of endothelial tight junction protein, JAM-A, in transendothelial migration of tumor cells leading to invasion and metastasis. The homophilic interactions of JAM-A molecules (both in cis- and trans-mode) form the zipper-like JAM-A homophilic adhesions and thus together with occludins, claudins, and cytoplasmic polarity complex molecules provide the structure of TJs. TJ is the most apical type of intercellular junctions that shows a certain selectivity and specificity for ions and molecules and thereby controls the permeability of endothelial barrier along the blood vessels. Inflammatory cytokines trigger JAM-A translocation from intercellular contacts toward the lumen of the vessels, thus enabling JAM-A interactions with the leukocyte surface proteins, including LFA-1, that consequently leads to the leukocyte TEM. It has been demonstrated that JAM-C dimerization is essential for tumor progression and metastasis in lung carcinoma, supporting similar observations for melanoma cells. These data led to the definition of the role of JAM-A in TEM of breast cancer cells and, subsequently, in mammary tumor metastasis induced by Tβ4 or inflammatory cytokines.

The present example began with in vivo experiments on the murine 4T1 breast cancer model. The mice were challenged with Tβ4. This actin-sequestering peptide is present in blood serum and plasma and has metastasis promoting activity. Moreover, the elevated levels of Tβ4 have been reported. TGF-β1 was used as a positive control for the downregulation of JAM-A level that was previously shown to induce the invasion breast cancer cell lines MCF-7 and MDA-MB-231.

The results of the in vivo example demonstrated that Tβ4 decreased the quantity of sJAM-A in murine blood in a mode similar to that of TGF-β1 (FIGS. 1a-1b). Furthermore, in vitro experiments on human endothelial cell line HMEC-1 have shown that both factors declined the JAM-A expression on protein, but not on mRNA level, as demonstrated by Western blot and RT-PCR, respectively (FIGS. 3a-3d). Flow cytometry data confirmed the results of Western blot analysis, but only the slight decrease of JAM-A level was observed on the surface of HMEC-1 cell treated by Tβ4 and TGF-β1 (FIGS. 4a-4d). Similarly, a nonsignificant increase of JAM-A level was noted on HMEC-1 surface upon TNF-α induction (FIGS. 4a-4d).

Therefore, the observed effect could be the result of decreased shedding of JAM-A, i.e. its release from the endothelial surface, while not of downregulated expression. JAM-A shedding occurs predominantly under inflammatory conditions and is mediated by two enzymes from the 'A disintegrin and metalloproteinase' (ADAM) family: ADAM10 and ADAM17. Soluble JAM-A limits the recruitment of inflammatory cells to sites of inflammation by blocking the TEM of neutrophils. The observed reduction of JAM-A shedding could be the effect of JAM-A relocalization from tight junctions to lysosomes driven by TGF-β1. Subsequently, JAM-A could be degraded in lysosomes, since the Western blot analysis demonstrated the decreased protein level of JAM-A (FIGS. 3a-3d).

TGF-β1 has dichotomous role in cancer progression, depending on the tumor stage. It has been shown to inhibit epithelial cell cycle progression and promote apoptosis, therefore acting as the tumor suppressor in early stage of carcinoma progression. However, TGF-β1 promotes epithelial to mesenchymal transition (EMT) that increases tumor cell motility and invasion, thus inducing metastasis. Moreover, TGF-β1 has been shown to suppress the antitumor activity of leukocytes, including neutrophils.

Tβ4 downregulated JAM-A level in the way similar to that one of TGF-β1. Tβ4 may induce the lysosomal proteolysis of JAM-A along the lines of TGF-β1. Tβ4 is overexpressed in various types of cancer, but in the presence of oxidizing agents Tβ4 sulfoxide is generated as a result of methionine residue oxidation at position 6. Tβ4 sulfoxide modulates the immune cells, downregulates NFκB, blocks the activity of IFN-γ and TNF-α and reduces the levels of multiple inflammatory chemokines and cytokines, including TNF-α and IFN-T. Therefore, the reduced level of JAM-A in plasma form Tβ4-treated mice could also result from the anti-inflammatory action of Tβ4 sulfoxide.

Figure 2B:
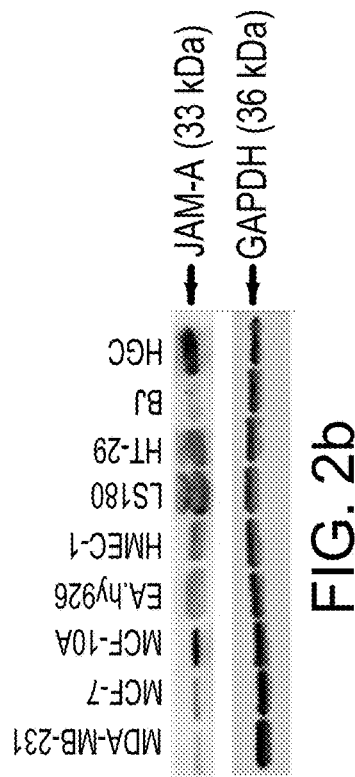
FIGS. 2a-2c are illustrations of real-time qRT-PCR (a) and Western blot (b) assay for detection of JAM-A expression levels using the RNA and protein extracts derived from the following human cell lines: breast cancer (MDA-MB-231 and MCF-7), non-cancerous MECs (MCF-10A), endothelial (EA.hy926 and HMEC-1), colorectal adenocarcinoma (LS180 and HT-29), skin fibroblasts (BJ) and primary cultured human glioma cells (HGC). Boxes plotted on panel (a) present the arithmetic means with minimum and maximum values (n=3). Statistically significant differences between the mean mRNA levels are presented in Supplementary Table S3. Panel (c): JAM-A (CD321) cell surface expression in non-tumorigenic MECs MCF-10A (black color) or in breast cancer cell lines (MCF-7, red color, and MDA-MB-231, green color) detected by flow cytometry.
Figure 2C:
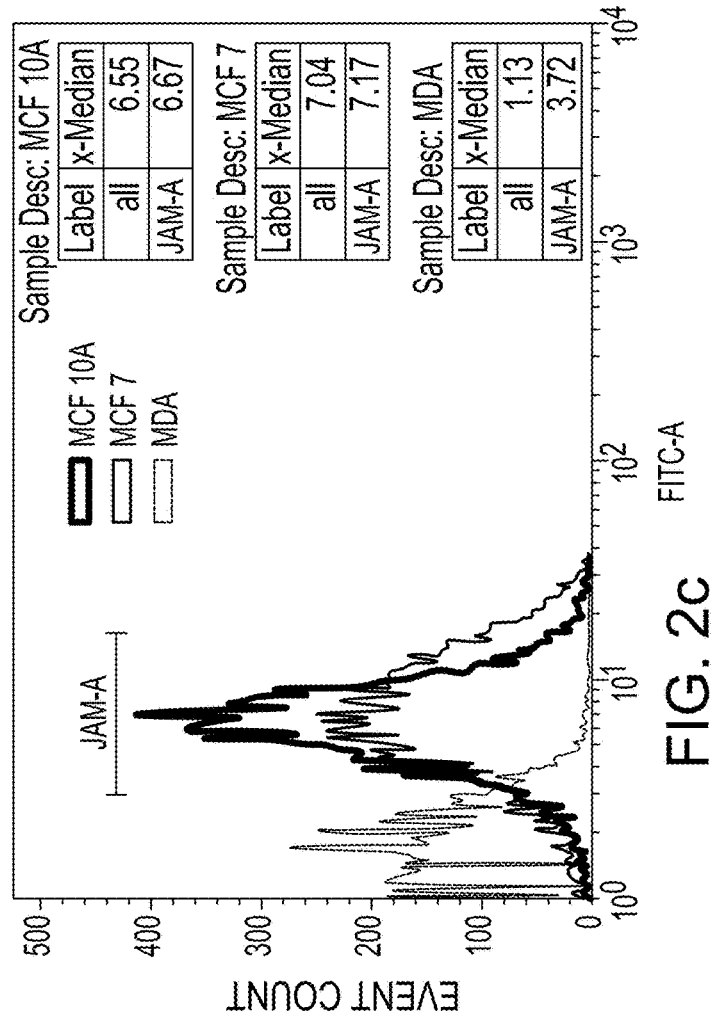
Figure 2A:
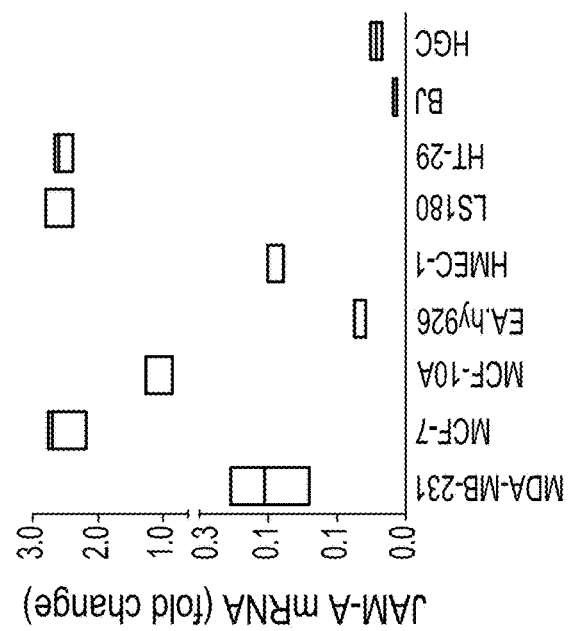

The observed lowered JAM-A expression level in MDA-MB-231 cells as compared with two other MEC lines (FIGS. 2a-2c) is in accordance with the previous reports showing, that the abundance of JAM-A negatively correlates with the metastatic potential of breast cancer cells. When analyzing the cell lines of other tissue origin, it was found that JAM-A expression on mRNA and protein level was elevated in tumor cell lines as compared to non-tumorigenic cells (FIGS. 2a-2c). In various types of cancer cells both underexpression and overexpression of JAM-A can be related to increased migration and invasion.

Soluble JAM-A is an inhibitor of TEM, thus, the decrease of its plasma level produced by Tβ4/TGF-β1 could result in the promotion of breast cancer cell extravasation. JAM-A has a prominent significance in cancer cell extravasation, since it is known to be present in early contacts points between the neighboring cells and adhesion is a substantial early step of extravasation that precedes TEM of leukocytes as well as TEM and subsequent metastasis of cancer cells. Moreover, TNF-α and IFN-γ were shown to upregulate lymphocyte adhesion to endothelial monolayer, thus triggering TEM with an active involvement of JAM-A. Consequently, the Peptide 4, as well as its D-amino acid analog (P4D) disclosed in U.S. Pat. No. 9,556,235, which is incorporated by reference, inhibits the trans-dimerization of JAM-A molecules was used to assess the role of JAM-A in the adhesion of MECs to endothelial monolayer.

Figure 5A:
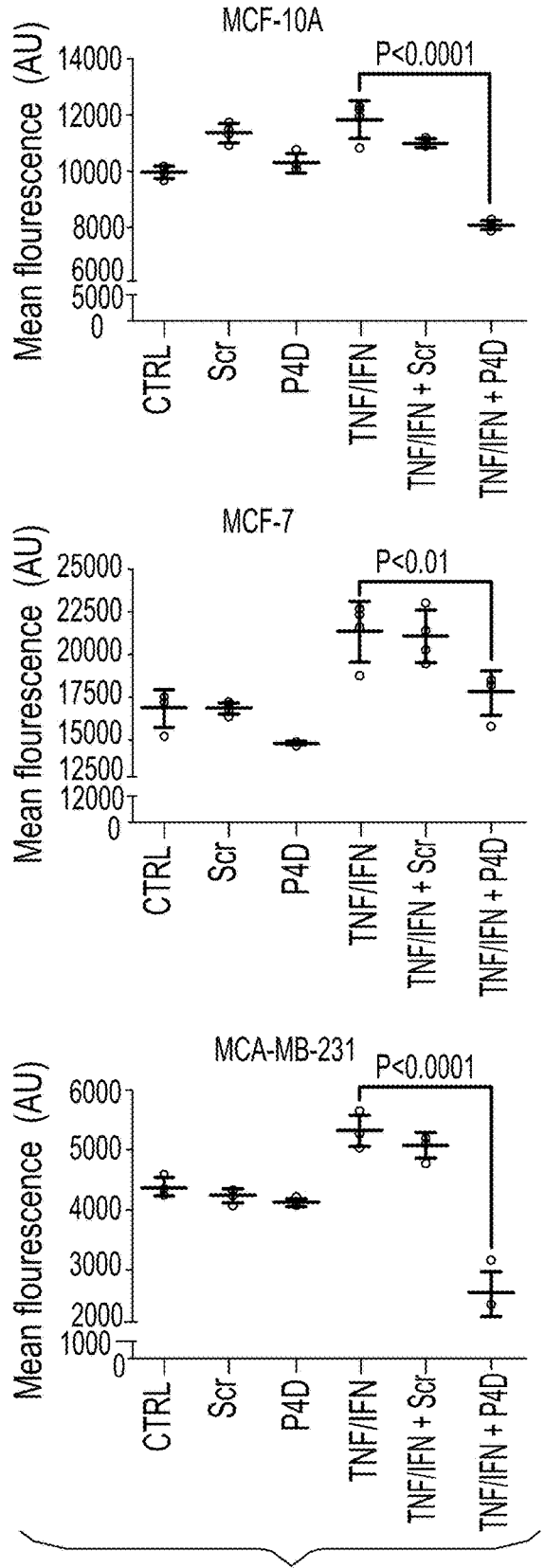
FIGS. 5a and 5b are illustrations of the effect of JAM-A inhibitory peptide P4D on breast cancer cells interactions with endothelium. Left panel (a): Adhesion of breast cancer cells to HMEC-1 cells. Results are expressed as mean fluorescence of adhered cells ±SD (n=4). Right panel (b): TEM of breast cancer cells. The plots present the mean values of migrated cell number per field of view ±SD (n=15). CTRL: control sample (untreated cells); Scr: Scrambled P4D peptide and P4D: JAM-A blocking peptide (500 μM, 4-hrs incubation); TNF/IFN: preincubation with TNF-α (10 ng/ml) and IFN-γ (20 ng/ml) for 24 hours before the treatment with P4D peptides; Tβ4: preincubation with Tβ4 (200 nM) for 24 hours before the treatment with P4D peptides.

This was done to estimate whether P4D would be able to inhibit the adhesion of breast cancer cells to the inflamed endothelium. The results of static adhesion assay have shown, that proinflammatory cytokines TNF-α and IFN-γ elevated the adhesion of breast cancer cells to endothelial monolayer, but this effect was blocked by P4D (FIG. 5a). The observed inhibitory action of P4D was particularly evident for MDA-MB-231 cells. FIGS. 2a-2c shows that this breast cancer cell line expresses low JAM-A levels as compared with other MECs, including another breast cancer cell line, MCF-7. This can be the result of the differences in the amount of JAM-A targeting microRNA, namely miR-495, in these cell lines. Correspondingly, it was reported to be expressed in high level in MDA-MB-231 cells, whereas MCF-7 cells were demonstrated to express miR-495 in lower quantity. Due to the lower JAM-A expression MDA-MB-231 cells were more sensitive to the blocking action of P4D, that resulted in more notably downregulated adhesion.

Figure 5B:
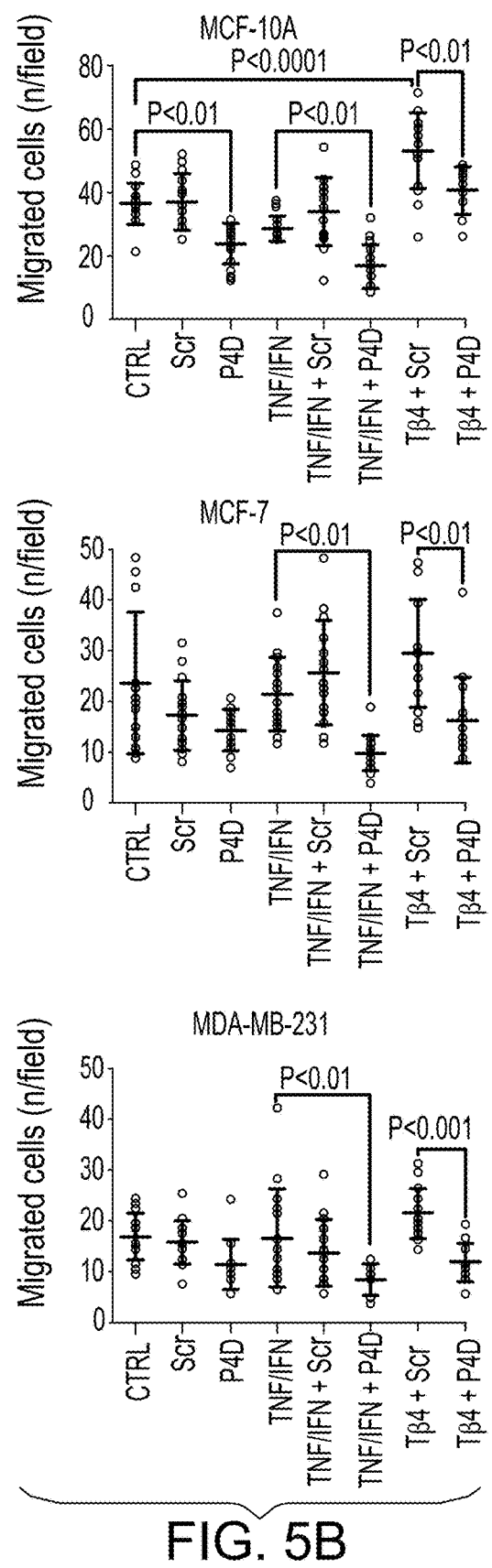

As previously reported, lower JAM-A expression in MDA-MB-231 cells contributes to their higher migratory abilities when compared with MCF-7 cells. P4D peptide suppressed TEM of MECs across the inflamed endothelium (FIG. 5b and FIG. 7). Inflammatory cytokines stimulated TEM of breast cancer cells more profoundly, than that of MCF-10A cells. Consequently, the inhibitory effect of P4D was more evident for breast cancer cell lines. However, the highest degree of TEM inhibition by P4D was observed for MCF-7 cells (FIG. 5b), those express high amounts of JAM-A. This is contradictory with the reported inverse relation between the JAM-A expression and migratory ability of breast cancer cells and supports the findings showing that JAM-A drives the breast cancer cells migration.

Moreover, P4D inhibited not only the TEM across inflamed endothelium, but also abrogated TEM of breast cancer cells, when the endothelial monolayer was activated with Tβ4 (FIG. 5b). It suggests, that P4D can prevent breast cancer metastasis triggered by diverse factors, since Tβ4 is a potent activator of cellular motility and tumor metastasis. Surprisingly, inflammatory cytokines and Tβ4 upregulated TEM of potentially non-malignant MCF-10A cells. This supports the observations, that MCF-10A cells may not represent a suitable model for normal, non-tumorigenic mammary epithelium.

It was reported that only certain types of anti-JAM-A antibodies could inhibit TEM of monocytes depending of which epitope was recognized and subsequently blocked. Accordingly, P4D inhibited breast cancer cell extravasation by: (1) reduction of adhesion of MECs to inflamed endothelium, and (2) downregulation of MECs transmigration across the endothelial monolayer. Thus, P4D can be used to restore the function of sJAM-A when this CAM is internalized and degraded in lysosomes. It appears that it was the trigger of decreased sJAM-A level in Tβ4- and TGF-β1-treated mice.

Figure 6A:
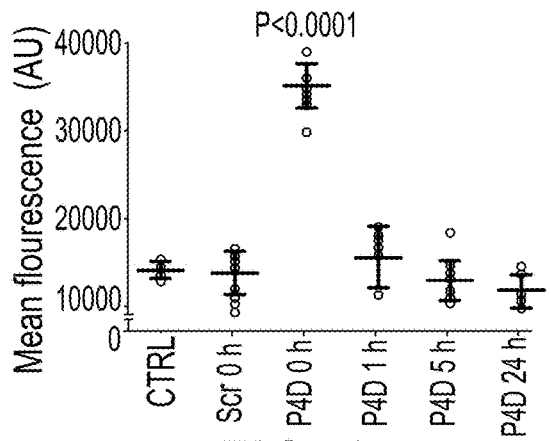
FIGS. 6a-6f are illustrations of the permeability of HMEC-1 endothelial monolayer. (a): Transendothelial flux of 40-kda FITC-dextran across HMEC-1 monolayer was measured with a Transwell two-compartment system. HMEC-1 cells were treated with P4D peptide or with Scrambled P4D peptide (Scr) at a concentration of 500 μM at the specified periods of time after seeding. Non-treated cells served as a control sample (CTRL). The plot presents the arithmetic means±SD (n=12). Graphs on panels (b)-(f) present the results of impedance-based real time measurements of HMEC-1 monolayer permeability shown as the time courses of cytokine-induced and compound-induced alterations of CI levels. (b): HMEC-1 cells were treated with the tested compounds (P4D, Scr, or FSK) ca. 24 hours after plating. (c): HMEC-1 monolayer was subjected to cytokine (TNF/IFN) treatment ca. 48 hours after seeding and subsequently to compounds treatment ca. 72 hours after seeding. (d)-(f): about 2.5 hours after seeding HMEC-1 cells were subjected to the compounds treatment followed by the cytokine treatment ca. 67 hours after plating. Panel (e) presents the detailed view of CI levels alterations after the compounds treatment, whereas panel (f) emphasizes the effect of cytokines on the changes of CI values after the compounds pretreatment for >60 hours. P4D & TNF/IFN: ca. 2.5 hours after seeding the cells were treated with P4D and next ca. 67 hours after plating the cells were subjected to the concurrent treatment with P4D and cytokines.

Noteworthily, endothelial permeability analysis by FITC-dextran flux showed that P4D peptide abrogated the formation of new TJs without the breakdown of pre-existing ones (FIG. 6a). RTCA analysis confirmed, that P4D has minor effect on endothelial barrier function when tight junctions have already been formed. No endothelial monolayer breakdown by P4D was observed. Moreover, P4D revealed the barrier-protecting effect. However, it was more potent than that of FSK only when P4D was applied shortly after a cytokine treatment and P4D stimulation was repeated with a booster dose (FIGS. 6b-6f). As previously shown using the analogous experimental approach, namely macromolecular fluorescent tracer flux and RTCA system, glycosylation at the residue N185 is critical for the ability of JAM-A to increase barrier function. Whereas the first Ig-Fold of JAM-A molecule is responsible for homodimerization, the second Ig-like domain, where N185 resides, is implicated in stabilization of homodimers. Consequently, N185 glycosylation was shown to regulate formation of JAM-A dimers.

N185S is reported as a somatic mutation in breast cancer in the Catalogue of Somatic Mutations in Cancer (COSMIC) database. A study on four human cancer cell lines reported that decreased expression of JAM-A contributes to enhanced epithelial permeability and subsequently to breast cancer cell invasion and metastasis. However, it was measured (using an EVOMX epithelial volt-ohm meter) the transepithelial resistance (TER) of MDA-MB-231 cells monolayer only, whereas transendothelial resistance was not assessed. Furthermore, ability to migrate and invasive potential of breast cancer cells was evaluated only in collagen gel and Matrigel.

The interactions of JAM-A molecules on the surface of breast cancer cells and endothelium were not taken into account since the transmigration of cancer cells across the endothelial monolayer was not estimated. Therefore it is important to note, that during this study of Naik et al. the metastatic potential of breast cancer cells was omitted. Thus, loss of JAM-A expression cannot be used as a direct prognostic marker for metastatic breast cancer.

The increase of endothelial permeability leading to upregulation of breast cancer cell line MDA-MB-231 invasiveness was also observed upon the stimulation with hepatocyte growth factor/scatter factor (HGF/SC). On the other hand, JAM-A overexpression resulted in decreased permeability of CHO cells monolayer as evaluated by FITC-dextran flux.

Decreased TER measured with a horizontal Ussing chamber was observed in the samples from patients suffering from allergic fungal rhinosinusitis. Increased epithelial permeability resulted here from JAM-A protein downregulation as shown by Western blot and immunofluorescence. Later the same group performed TER measurements with EVOM epithelial volt-ohm meter on sinonasal epithelial layers cultured from chronic rhinosinusitis patients. Inflammatory cytokines interleukin-4 and interleukin-13 downregulated JAM-A protein level as shown by Western blot and immunofluorescence, reflecting increased epithelial permeability. However, the fluctuations of JAM-A mRNA level are not reported.

In another study, miR-146a-induced JAM-A overexpression increased the barrier function of human nasal epithelium (as evaluated by TER measurement with EVOM) with the concurrent decrease of inflammatory response by prevention of interleukin-8 and TNF-α release, thus it reversed the action, that was previously reported for poly(I:C). Besides, endothelial and epithelial barrier function is controlled by JAM-A in the human eye. JAM-A antibody increased dextran flux across the retinal pigment epithelium. Decreased JAM-A expression was shown to be crucial in the pathogenesis of diabetic eye disease, since it contributed to the increase in retinal endothelial cell permeability as measured by macromolecular tracer assay.

The ACEA xCELLigence RTCA system was reported to dynamically record the possible impacts of six HIV-1 latency-reversing agents on the brain microvascular endothelial monolayer resistance (in vitro model of blood-brain barrier integrity and permeability). Two tested compounds, prostratin and bryostatin-1, reduced the JAM-A expression, as evidenced by immunofluorescence microscopy. This triggered a breakdown of endothelial integrity and simultaneous enhancement of monocyte adhesion to endothelial monolayer, but TEM of monocytes was markedly reduced. For comparison, in the present experiments, P4D inhibited adhesion and TEM of breast cancer cells (FIGS. 5a-5b) and simultaneously preserved the endothelial barrier function (FIGS. 6a-6f).

Figure 6B:
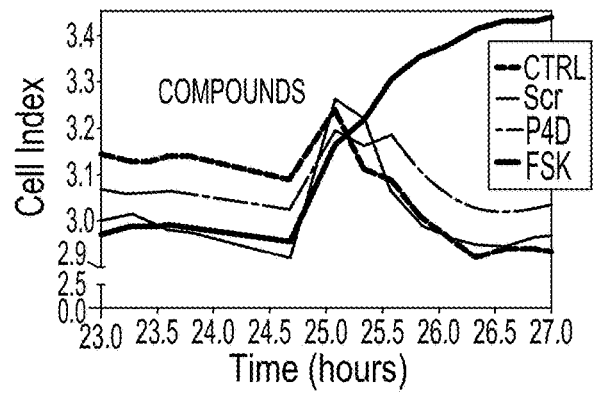
Figure 6C:
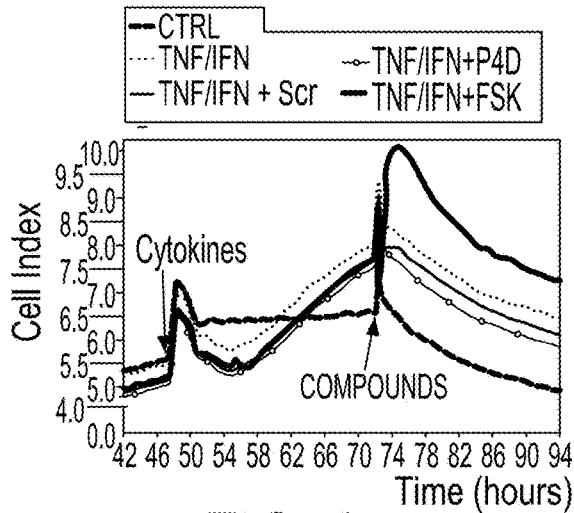

By RTCA analysis it was confirmed the previous reports proving, that proinflammatory cytokines increase the permeability of endothelial barrier, as evidenced by the reduced resistance of cellular monolayer (FIG. 6c). This is in accordance with other papers showing the results of impedance- or resistance-based measurements of endothelial/epithelial barrier function.

For instance, the chemokine (C—C motif) ligand 2 (CCL2)- or lipopolysaccharide (LPS)-induced increases in brain endothelial cell barrier permeability were documented by the drop of TEER measured with an EVOM device that was coincident with JAM-A redistribution from the interendothelial cell border to the apical surface of brain endothelial cells. In human umbilical vein endothelial cells (HUVECs) TNF-α induced RhoA activation and myosin light chain phosphorylation, and subsequently caused a progressive increase in permeability (measured by FITC-dextran flux) and in stress fiber reorganization, cell elongation, and intercellular gap formation. Consistent with the increased permeability, JAM-A was removed from tight junctions and was distributed diffusely, suggesting that JAM-A was redistributed over the cell membrane and/or internalized. Furthermore, TNF-α in tandem with TGF-β3 significantly accelerated the kinetics of JAM-A internalization by clathrin-mediated endocytosis as shown by TER measurement in a primary Sertoli cell culture that formed a functional blood-testis barrier.

Nevertheless, proinflammatory cytokines do not always disrupt the integrity of TJs. In other studies, the established primary cultures of human submandibular gland epithelial cells from patients with IgD4-related disease (IgG4-RD) and control individuals. As evidenced by TER measurements with EVOM instrument, IFN-γ significantly increased the epithelial barrier function in samples from patients with IgG4-RD and from healthy volunteers. In contrast, TGF-β dramatically decreased TER of salivary gland duct epithelium.

Example 2

All in vivo experiments were carried on female BALB/c mice aged 8 to 12 weeks purchased from Animal House of Institute of Biology, University of Bialystok (Bialystok, Poland). The mice were housed under standard conditions at the Animal House of the Medical University of Lodz (Lodz, Poland). All animal procedures and protocols were conducted in accordance with the Guide for the Care and Use of Laboratory Animals of the National Animal Care Committee and were approved by Local Ethical Committee for Animal Research in Lodz (license number 9/LB51/2017 from Jun. 2, 2017). All efforts were made to minimize animal suffering.

Mice Mammary Gland Tumor Culture and Tumor Induction

Murine 4T1 cells were purchased from the American Type Culture Collection (ATCC, Manassas, Va., USA). The cells were maintained in RPMI-1640 (ATCC) with 10/o fetal bovine serum (FBS) and cultured in tissue culture flasks to 80% confluence. 4T1 cells were harvested from the culture flasks, resuspended in a number of $10^4$ cells in 100 μL PBS per mouse and administrated subcutaneously in inguinal nipple area.

Chemotherapy

Seven days after 4T1 cells injection the mice were divided into three groups, and each group were given different chemotherapeutic: Tβ4 (Bachem, Switzerland), TGF-β1 (R&D Systems, USA) or vehicle (PBS, control group). Briefly, non-control groups were given intraperitoneally Tβ4 or TGF-β1 resuspended in PBS in a concentration of 15 μg/1 kg body weight or 5 μg/1 kg body weight, respectively. Chemotherapy was conducted according to the following schedule: one chemotherapeutic injection followed by three days of break. After 21 days of chemotherapy mice were anesthetized intraperitoneally with ketamine (Biowet, Pulawy, Poland) and xylazine (Biowet, Pulawy, Poland) solution (0.1 mL/20 g mouse). Blood samples were collected from mice by cardiac blood draw using a syringe with K2-EDTA solution (Sigma Aldrich, USA). Samples were next centrifuged at 662G for 10 min at 4° C., the resulting plasma was aliquoted and stored at −80° C. for further analysis.

Cell Culture

MCF-10A (non-tumorigenic human breast epithelium), MCF-7 (human breast adenocarcinoma, molecular classification: Luminal A), MDA-MB-231 (human breast adenocarcinoma, molecular classification: Claudin-low) and HMEC-1 (human microvascular endothelial) cell lines were purchased from the ATCC. MCF-10A is a cell line used as a model of non-tumorigenic epithelial cells from human mammary gland. MCF-7 and MDA-MB-231 cells are of epithelial morphology and represent the model of human mammary gland adenocarcinoma. HMEC-1 cells are the human microvascular endothelial cell line derived from dermal microvascular endothelium. MCF-10A cells were grown in MEBM supplemented with MEGM Single Quots and cholera toxin (Lonza, Basel, Switzerland). MCF-7 and MDA-MB-231 cells were cultured in RPMI-1640 medium supplemented with 10% fetal bovine serum (FBS). HMEC-1 cells were grown in MCDB 131 medium supplemented with 10 ng/mL epidermal growth factor (EGF), 1 μg/mL hydrocortisone, 10 mM glutamine and 10% FBS. All the cell lines were cultured in a humidified incubator in the temperature of 37° C. and atmosphere with 5% $CO_2$. Confluent cells were passaged using trypsin-EDTA at a split ratio of 1:4 (MCF-10A, MCF-7, MDA-MB-231) or 1:10 (HMEC-1). The culture media were changed each 2-3 days.

Cell Treatment

Before the experiments, the cells were cultured overnight in Opti-MEM Reduced Serum Medium (Gibco, Waltham, Mass., USA). Subsequently, the cells were incubated for 0, 2, 5, 12, or 24 hours with Tβ4 at a concentration of 200 nM, for 24 hours with TGF-β1 at a concentration of 10 ng/mL, for 24 hours with tumor necrosis factor-α (TNF-α) at a concentration of 10 ng/mL, or for 24 hours with a mixture of proinflammatory cytokines (TNF/IFN): TNF-α (10 ng/mL) and interferon-γ (IFN-γ; 20 ng/mL); in a cell culture medium without serum. For the inhibition of JAM-A homophilic interactions and TJ formation the cells were treated with the F11R P4D peptide that blocks trans-homodimerization of JAM-A molecules. Consequently, the P4D peptide inhibits the formation of TJ in the endothelial monolayer as well as between the cancer cells and endothelial cells. The sequence of P4D peptide is based on the 70-82 amino acids fragment of the F11R polypeptide chain that is located in the first immunoglobulin-fold (Ig-Fold) of the protein's mature molecule which does not include the 27 amino acid leader peptide sequence.

The peptides were synthesized and purified by LifeTein, LLC (Somerset, N.J., USA) with the purity of not less than 95% using PeptideSyn™ technology that incorporates solid phase fluorenylmethyloxycarbonyl (Fmoc) chemistry. The cells were treated with the peptide P4D for 0, 1, 5, or 24 hours at a concentration of 500 µM. The cells treated with the Scrambled peptide P4D (Scr; 500 µM; 0, 1, 5, or 24 hours incubation time) were used as a negative control. In order to provide the positive control of the junctions tightening for impedance-based measurements of endothelial permeability, the cells were incubated with the potent activator of TJ assembly, forskolin (FSK; BioShop, Burlington, ON, Canada), for 24 hours at a concentration of 10 µM.

Enzyme-Linked Immunosorbent Assay

For enzyme-linked immunosorbent assay (ELISA) analyses the samples from murine plasma were diluted 20-fold in a dilution buffer provided by a manufacturer of a corresponding ELISA kit. Tβ4 antigen level measurements in murine plasma were performed by Mouse Thymosin beta-4 ELISA Kit (Biomatik, Canada) according to manufacturer's protocol based on the competitive binding enzyme immunoassay technique. During the reaction, Tβ4 (target antigen) in the standards or sample solutions competed with a fixed amount of biotin-labeled Tβ4 for binding sites on the 96-well microtiter plate pre-coated with an Tβ4-specific monoclonal antibody.

Excess conjugate and unbound target antigen in the standards or samples are washed from the plate and subsequently, avidin conjugated to horseradish peroxidase (HRP) was added to each microplate well. After the plate was incubated with avidin-HRP, the TMB (3, 3, 5, 5'-tetramethylbenzidine) substrate solution was added to each well. JAM-A antigen level measurements in murine plasma were performed by RayBio® Mouse JAMA ELISA Kit (RayBiotech, USA) according to manufacturer's protocol. Briefly, standards and samples were applied into the wells of a 96-well microplate pre-coated with an antibody specific for mouse JAM-A. The wells were washed and subsequently the biotinylated anti-mouse JAM-A antibody was added.

The unbound biotinylated antibody was washed away and HRP-conjugated streptavidin was added to the wells. After another wash, a TMB substrate solution was added to the wells. Regarding the both protocols, the enzyme-substrate (HRP-TMB) reaction was terminated by the addition of a sulfuric acid solution and the color change was measured spectrophotometrically at a wavelenght of 450 nm using the Wallac 1420 VICTOR2 Multilabel Counter (PerkinElmer). The concentration of target antigen in the samples was determined by comparing the optical density of the samples to the standard curve.

Quantitative Real-Time RT-PCR (QRT-PCR)

The cells were harvested with TriPure Reagent (Roche Applied Science, Mannheim, Germany) for the total RNA isolation due to the manufacturer's protocol. The obtained RNA pellets were dissolved in nuclease-free water. Concentration and purity of RNA was determined by spectrophotometer readings at 260 and 280 nm. Subsequently, the RNA concentrations in all samples was equalized and the RNA (0.5 µg per sample) was transcribed to cDNA using the iScript cDNA synthesis Kit (Bio-Rad, Hercules, Calif., USA) according to the manufacturer's instructions. After reverse transcription, the obtained cDNA samples were quantified by real-time PCR using iTaq Universal SYBR Green Supermix (Bio-Rad) and the CFX Connect Real-Time System (Bio-Rad). Each sample containing 1 µL of cDNA was supplemented with both respective 0.25 µM forward and reverse primers, 10 µL of iTaq Universal SYBR Green Supermix with nuclease-free water to make up to 20 µL. The specific oligonucleotide primer pairs were synthesized (Genomed, Warsaw, Poland) and subsequently used in PCR reactions for the following transcripts: forward 5'-CGA-GAGGAAACTGTTGTGCC-3' (SEQ ID NO: 5 and reverse 5'-AACGAGTCTGGTGGTGTCTC-3' (SEQ ID NO: 6) for JAM-A (199 base pairs product length), forward 5'-CTTTTCCTCCGCAACCATGT-3' (SEQ ID NO: 7) and reverse 5'-AGGGGCAGCACAGTCATTTA-3' (SEQ ID NO: 8) for Tβ4 (279 bp product length), as well as forward 5'-GAGAGATGATGACCCTTTTGGC-3' (SEQ ID NO: 9) and reverse 5'-CCATCACCATCTTCCCAGGAGCG-3' (SEQ ID NO: 10) for glyceraldehyde 3-phosphate dehydrogenase (GAPDH; 160 bp product length). GAPDH transcript was used as an endogenous reference to correct for differences in the amount of total RNA added to the reaction and to compensate for different levels of inhibition during reverse transcription of RNA and during PCR.

Each sample was amplified in triplicate and at last three separate experiments were quantified in an individual 96-well plate. All samples were incubated at 95° C. for 3 min and then cycled at 95° C. for 10 s and 55° C. for 30 s for 40 cycles. SYBR Green I fluorescence emission data were captured and mRNA levels were quantified using the critical threshold (Ct) value. Analyses were performed with CFX Manager software, version 3.1 (Bio-Rad). Controls without reverse transcription and with no template cDNA were performed with each assay. To compensate for variations in input RNA amounts, and efficiency of reverse transcription, GAPDH mRNA was quantified and results were normalized to these values. The relative mRNA expression levels were estimated using the $2^{-\Delta\Delta Ct}$ quantification method. Ratios of the amounts of mRNA from stimulated and untreated cells were calculated.

Amplifications of specific transcripts were further confirmed by obtaining melting curve profiles. Alternatively, the amplified products were separated by electrophoresis in 7% polyacrylamide gels in Tris-acetate-EDTA buffer (TAE; tris (hydroxymethyl)aminomethane; ethylenediaminetetraacetic acid) using the genetic size marker 100-base pair (bp) DNA ladder (Promega). Bands were visualized by ethidium bromide and UV light, recorded photographically using Gel Doc 2000 Gel Documentation System (BioRad) and analyzed densitometrically by the ImageJ software, version 1.49h (National Institute of Health, USA).

Western Blot

The cells were lysed with lysis buffer (1% Triton X-100 and 0.1% SDS in PBS) supplemented with Halt Protease Inhibitor Cocktail (Thermo Scientific, Waltham, Mass., USA). For the equalization between the samples before the semi-quantitative analyses the protein content of lysates was determined with the BCA Protein Assay Kit according to the manufacturer's protocol (Thermo Scientific). Cell lysate aliquots at a protein content of 50 μg per sample were boiled with 5× concentrated loading buffer (final concentrations: 50 mM Tris-HCl, pH 6.8, 8% glycerol, 2% SDS, 5% β-mercaptoethanol, 0.002% bromophenol blue), separated under reducing conditions on 4-20% gradient SDS-PAGE gels (Bio-Rad) and electroblotted (120 min, 200 mA, 4° C.) onto polyvinylidene difluoride (PVDF) membranes (Bio-Rad). The membranes were washed with Tris-buffered saline (TBS) and blocked for 2 hours with TBS containing 5% nonfat dry milk at room temperature. Then, the membranes were incubated overnight at 4° C. with an appropriate amount of primary antibody diluted in TBS containing 0.05% Tween 20 (TBST). The following primary antibodies were used: monoclonal rabbit anti-JAM-A (Abcam, Cambridge, UK) at a dilution of 1:500 and monoclonal mouse anti-GAPDH (R&D Systems, Minneapolis, Minn., USA) at a dilution of 1:1000. The membranes were washed several times with TBST and incubated for 1 hour at room temperature with the corresponding polyclonal anti-rabbit and anti-mouse HRP-conjugated secondary antibodies (Santa Cruz Biotechnology, Dallas, Tex., USA) at a 1:5000 dilution in TBST. Following the subsequent washes with TBST the membranes were further processed for chemiluminescent detection using Westar TiC ECL Substrate (Cyanagen, Bologna, Italy) and the images were documented by ChemiDoc MP Imager (Bio-Rad). Densitometric analysis was performed with ImageJ software, version 1.49h (National Institute of Health, USA). GAPDH bands served as loading controls.

Flow Cytometry

For the detection of JAM-A surface expression the cells were labeled with FITC anti-human CD321 (F11R) Mouse $IgG_1$ Antibody (BioLegend, San Diego, Calif., USA) or with the FITC Mouse $IgG_1$ Isotype Control Antibody (BioLegend) for the negative control. Labeled cells were washed to remove unbound antibodies, harvested with ice cold EDTA/PBS, fixed with BD CellFix (Becton Dickinson. Franklin Lakes, N.J., USA) and subsequently analyzed by FACS Canto II flow cytometer (Becton Dickinson). Upon excitation at 488 nm with an argon laser the emission of the fluorescence was recorded through selective band pass filter at 517 nm. Data were recorded with DIVA software, version 6.0 (Becton Dickinson) and subsequently analyzed using FCSalyzer software, version 0.9.14-alpha (https://sourceforge.net/projects/fcsalyzer/).

Adhesion of Breast Cancer Cells to Endothelial Monolayer Under Static Conditions Adhesion of human breast cancer (MCF-7, MDA-MB-231) or non-tumorigenic (MCF-10A) human breast cells to HMEC-1 cells was performed in 24-well plates. HMEC-1 cells were seeded to the bottom of the fibronectin-coated wells 2 days before the assay to form the monolayer and subjected to a suitable treatment. Breast cancer or non-tumorigenic cells were starved overnight and on the day of the assay were labeled with CellTracker Green CMFDA Dye for 30 minutes. Just before the assay the HMEC-1 cells culture medium was substituted with the adhesion medium (MCDB 131 containing 1 mM $CaCl_2$, 1 mM $MgCl_2$ and 1% bovine serum albumin). Subsequently the aliquots of breast cancer or non-tumorigenic cells ($1 \times 10^5$/well) were applied onto the endothelial monolayer and allowed to adhere at a presence of an appropriate factor for 1 hour in a humidified incubator with 5% $CO_2$ and the temperature of 37° C. Non-adherent cells were washed away by 3 washes of PBS. The adherent cells were lysed by 2% SDS and the fluorescence was measured using the Wallac 1420 VICTOR2 Multilabel Counter (PerkinElmer) at 492 nm of excitation and 517 nm of emission wavelengths.

Transmigration of Breast Cancer Cells Across the Endothelial Monolayer

HMEC-1 endothelial cells were cultured in fibronectin-coated Transwell units with polycarbonate filter and 8 μm pores (Costar, Corning, N.Y., USA) in 24-well plates for 2 days at 37° C. to form a confluent monolayer. Human breast cancer (MCF-7, MDA-MB-231) or non-tumorigenic (MCF-10A) human breast cells were starved overnight and labeled with the green fluorescent marker CellTracker Green CMFDA Dye (Molecular Probes, Eugene, Oreg., USA). An aliquot ($1 \times 10^5$/well) of fluorescent breast cancer cells in serum-free medium was added in the top of the Transwell chamber, whereas the conditioned medium was used as a chemoattractant in the lower compartment. Non-tumorigenic human breast cell line MCF-10A was used as control. The wells containing the serum-free medium in the lower compartment were used to estimate the background migration. The breast cancer cells were allowed to migrate across the endothelial monolayer for 6 hours in a humidified incubator (temperature of 37° C. and 5% $CO_2$ atmosphere) with or without the previously specified factors or with their combinations.

At the end of the transmigration assay, non-migrated cells were gently wiped out from the inner surface of the membrane with cosmetic cotton swab. The assay was documented at 200× magnification (10× eyepiece and 20× objective) with fluorescent inverted microscope Axio Vert.A1 (Zeiss, Oberkochen, Germany) and high-performance CMOS 2.3-MP AxioCam 702 mono digital camera (Zeiss) controlled by ZEN software, version 2.3 (Zeiss). The migrated cells (five randomly chosen fields of each well) were counted using the Cell Counter tool of the ImageJ software. Cell migration towards serum-free medium was treated as background and subtracted from the corresponding numbers of cells migrated towards conditioned medium.

Macromolecular Permeability of Endothelial Monolayer

Macromolecular permeability of endothelial monolayer was analyzed by macromolecular tracer assay. HMEC-1 cells were grown in Transwell inserts with polyethylene terephthalate (PET) filters and 0.4-μm pores (Falcon, cat. #353095) in 24-well plates (Falcon, cat. #351147) at $1.5 \times 10^5$ cells/insert and immediately treated with P4D peptide (P4D) or with Scrambled P4D peptide (Scr) at a concentration of 500 μM (the samples indicated as 0 hours of incubation). Non-treated cells served as a control sample (Ctrl). Moreover, HMEC-1 cells were treated with P4D peptide at the following periods of time after seeding: 1 hour, 5 hours and 24 hours. One hour after the last treatment with P4D (24 hours) FITC-dextran with a molecular weight of 40 kDa was added into the inserts and the culture medium from the wells was replaced with PBS. After 1 hour incubation in darkness in a humidified incubator with the temperature of 37° C. and 5% $CO_2$ atmosphere, the PBS from the wells (outside the inserts) was transferred into the wells of a black 96-well plate and the fluorescence was measured using the Wallac 1420 VICTOR2 Multilabel Counter (PerkinElmer, Waltham, Mass., USA) at 492 nm of excitation and 517 nm of emission wavelengths.

Impedance-Based Measurement of Endothelial Permeability

Experiments based on impedance measurements were performed at Bionanopark, Ltd. (Lodz, Poland) with an ACEA xCELLigence® Real-Time Cell Analysis (RTCA) DP system (Roche, Mannheim, Germany) consisting of an RTCA DP instrument, a personal computer-based RTCA control unit and single-use electronic 16-well plates "E-Plate VIEW 16 PET". All experiments were performed following the manufacturer's instructions. In brief, the gold-film electrodes deposited on the bottom of the "E-plate VIEW 16 PET" electrode arrays were equilibrated with MCDB 131 culture medium overnight. Subsequently, the medium was aspirated and replaced by a 100 µL of fresh medium for impedance background measurements. HMEC-1 cells were seeded at a density of 40,000 cells per well in MCDB 131 medium with supplements. After allowing cell sedimentation for 30 min at room temperature, plates were locked into the RTCA DP instrument for continuous recording of impedance changes at three different AC frequencies (10 kHz, 25 kHz, 50 kHz), which are expressed as Cell Index (CI) values. CI is a dimensionless parameter based on relative impedance changes referenced to the values of the cell-free electrode at each frequency:

$$CI = \max_{i=1,\ldots,N}\left(\frac{R_{cell}(fi)}{R_b(fi)} - 1\right)$$

where N is the number of the frequency points at which the impedance was measured, whereas $R_{cell}(fi)$ and $R_b(fi)$ are the frequency-dependent electrode resistances with cells present and without cells, respectively. Thus, CI is a quantitative measure of cell status in a well, including the cell number, cell viability, adhesion degree, and morphology. Although CI is measured at three frequencies, only the most sensitive readings are returned by the software as a function of time and reported as the final results. In general, CI values rise with increasing coverage of the electrode with cells, which is caused at an early stage by cell sedimentation and, later on, by cell proliferation. During the phase of logarithmic cell growth HMEC-1 cells were pretreated with cytokines (TNF/IFN) and after 24 hours subsequently treated with the tested compounds (Scr, P4D, or FSK). For some experiments, the cells were treated with the compounds 2 hours after the cytokines treatment. Alternatively, the compounds treatment was applied about 3 hours after HMEC-1 seeding and about 67 hours later was followed by the cytokines treatment. This experimental approach included additionally the sample designated as 'P4D & TNF/IFN' i.e. after the pretreatment with P4D the cells were subjected to the concurrent treatment with P4D and cytokines.

Statistical Analysis

The results are presented as arithmetic mean±standard deviation (SD) of at last three independent experiments. The normality of the data distribution was verified by D'Agostino & Pearson omnibus K2 normality test. Subsequently, the data were analyzed by one-way ANOVA with the Tukey's post hoc multiple comparisons test. Differences were considered statistically relevant at the significance level P<0.05. Statistical analysis was performed using GraphPad Prism statistical software, version 6.01 (GraphPad Software, Inc., La Jolla, Calif., USA).

Results

Thymosin β4 (T β4) and Transforming Growth Factor-β1 (TGF-β1) Reduce the Plasma Level of Soluble JAM-A Observations in vivo were carried out in the murine 4T1 breast cancer model. Mouse mammary carcinoma cells of 4T1 cell line were transplanted into the mammary fat pad of the immune-competent BALB/c female mice. This model of breast cancer is characterized by a spontaneous metastasis into distant organs. Moreover, 4T1 tumor progression is accompanied by the development of endothelial dysfunction. Accordingly, 4T1 breast cancer model enables the simultaneous studies of broad range of metastasis aspects, notably the TEM of tumor cells. Blood plasma samples received from 4T1 tumor-bearing mice and the control littermates were analyzed by enzyme-linked immunosorbent assay (ELISA) for the Tβ4 and JAM-A quantitation (FIGS. 1a and 1b). T β4 levels did not differ in all samples with a non-significant tendency of an infinitesimal upregulation in 4T1 tumor-bearing mice (FIG. 1a and Table 1 below).

TABLE 1

| Tukey's multiple comparisons test | Probability value |
| --- | --- |
| CTRL/PBS vs. 4T1/PBS | 0.6076 |
| CTRL/PBS vs. CTRL/Tβ4 | 0.9991 |
| CTRL/PBS vs. 4T1/Tβ4 | 0.7947 |
| CTRL/PBS vs. CTRL/TGFβ1 | 0.9999 |
| CTRL/PBS vs. 4T1/TGFβ1 | 0.9996 |
| 4T1/PBS vs. CTRL/Tβ4 | 0.8223 |
| 4T1/PBS vs. 4T1/Tβ4 | 0.9996 |
| 4T1/PBS vs. CTRL/TGFβ1 | 0.4562 |
| 4T1/PBS vs. 4T1/TGFβ1 | 0.7890 |
| CTRL/Tβ4 vs. 4T1/Tβ4 | 0.9413 |
| CTRL/Tβ4 vs. CTRL/TGFβ1 | 0.9903 |
| CTRL/Tβ4 vs. 4T1/TGFβ1 | >0.9999 |
| 4T1/Tβ4 vs. CTRL/TGFβ1 | 0.6548 |
| 4T1/Tβ4 vs. 4T1/TGFβ1 | 0.9229 |
| CTRL/TGFβ1 vs. 4T1/TGFβ1 | 0.9943 |

In Table 1 above, the statistical analysis of Tβ4 antigen levels measured by ELISA in murine plasma (one-way ANOVA followed by Tukey's multiple comparisons test) are shown.

T β4 was found to decrease JAM-A level in plasma derived from mammary tumor-bearing mice as well as from the control littermates. Furthermore, TGF-β1 decreased the JAM-A plasma level in both tested groups (FIG. 1b). The tendency of slight JAM-A upregulation upon mammary tumor induction was also observed and it was more evident than the one for T β4, but statistical significance was shown only for the T β4-treated mice (P=0.0015; FIG. 1b and Table 2 below).

TABLE 2

| Tukey's multiple comparisons test | Probability value |
| --- | --- |
| CTRL/PBS vs. 4T1/PBS | 0.7766 |
| CTRL/PBS vs. CTRL/Tβ4 | <0.0001 **** |
| CTRL/PBS vs. 4T1/Tβ4 | 0.0048 ** |
| CTRL/PBS vs. CTRL/TGFβ1 | <0.0001 **** |
| CTRL/PBS vs. 4T1/TGFβ1 | <0.0001 **** |
| 4T1/PBS vs. CTRL/Tβ4 | <0.0001 **** |
| 4T1/PBS vs. 4T1/Tβ4 | <0.0001 **** |
| 4T1/PBS vs. CTRL/TGFβ1 | <0.0001 **** |
| 4T1/PBS vs. 4T1/TGFβ1 | <0.0001 **** |
| CTRL/Tβ4 vs. 4T1/Tβ4 | 0.0015 ** |
| CTRL/Tβ4 vs. CTRL/TGFβ1 | 0.8055 |
| CTRL/Tβ4 vs. 4T1/TGFβ1 | 0.9998 |
| 4T1/Tβ4 vs. CTRL/TGFβ1 | <0.0001 **** |
| 4T1/Tβ4 vs. 4T1/TGFβ1 | 0.0036 ** |
| CTRL/TGFβ1 vs. 4T1/TGFβ1 | 0.6440 |

In Table 2 above, the statistical analysis of JAM-A antigen levels measured by ELISA in murine plasma (one-way ANOVA followed by Tukey's multiple comparisons test). Statistically significant differences are marked with asterisks ( for P<0.01, and ** for P<0.0001).

Subsequently, a comparison was made between JAM-A mRNA and protein expression levels in human cell lines of diverse tissue origins. Particularly, the differences of JAM-A expression in tumorigenic and non-tumorigenic cells were analyzed. The data revealed that in tumor cell lines JAM-A expression on mRNA and protein level was higher as compared to non-cancerous cells (FIGS. 2a-2c). This effect was characterized with several discrepancies in the case of MECs. Qualitative RT-PCR data show that the lowest mRNA level of JAM-A was found in MDA-MB-231 cells as compared to the other MECs tested (FIG. 2a). JAM-A expression was slightly elevated in breast cancer cell line MCF-7 than in non-tumorigenic MCF-10A cells as demonstrated by qRT-PCR (FIG. 2a). Inversely, immunobloting analysis of the samples derived from MCF-10A cells revealed that JAM-A protein level was higher in this cell line as compared with MCF-7 and MDA-MB-231 protein extracts (FIG. 2b). Flow cytometry experiments confirmed the data of qRT-PCR, since the lowest JAM-A expression was found on the surface of MDA-MB-231 cells, whereas MCF-7 and MCF-10A cell lines expressed the similar levels of surficial JAM-A with only a slight increase observed for MCF-7 cells (FIG. 2c). In a summary, the lowest expression level of JAM-A mRNA and protein was observed in MDA-MB-231 cells, as compared with two other MECs. Statistical significances of differences between the results obtained after the qRT-PCR analysis are presented in Table 3 below.

TABLE 3

| Tukey's multiple comparisons test | Probability value |
| --- | --- |
| MDA-MB-231 vs. MCF-7 | <0.0001 **** |
| MDA-MB-231 vs. MCF-10A | 0.0003 *** |
| MDA-MB-231 vs. LS180 | <0.0001 **** |
| MDA-MB-231 vs. HT-29 | <0.0001 **** |
| MCF-7 vs. MCF-10A | <0.0001 **** |
| MCF-7 vs. EA.hy926 | <0.0001 **** |
| MCF-7 vs. HMEC-1 | <0.0001 **** |
| MCF-7 vs. BJ | <0.0001 **** |
| MCF-7 vs. HGC | <0.0001 **** |
| MCF-10A vs. EA.hy926 | <0.0001 **** |
| MCF-10A vs. HMEC-1 | 0.0002 *** |
| MCF-10A vs. LS180 | <0.0001 **** |
| MCF-10A vs. HT-29 | <0.0001 **** |
| MCF-10A vs. BJ | <0.0001 **** |
| MCF-10A vs. HGC | <0.0001 **** |
| EA.hy926 vs. LS180 | <0.0001 **** |
| EA.hy926 vs. HT-29 | <0.0001 **** |
| HMEC-1 vs. LS180 | <0.0001 **** |
| HMEC-1 vs. HT-29 | <0.0001 **** |
| LS180 vs. BJ | <0.0001 **** |
| LS180 vs. HGC | <0.0001 **** |
| HT-29 vs. BJ | <0.0001 **** |
| HT-29 vs. HGC | <0.0001 **** |

Table 3 includes data regarding TEM of breast cancer cells, which are microscopic photographs presenting the fluorescently labeled breast cancer cells (MCF-7, MDA-MB-231) or non-tumorigenic MECs (MCF-10A) those transmigrated across the endothelial monolayer. The corresponding plots and detailed specifications are shown in FIG. 5b.

Figures 3A, 3B, 3C, 3D:
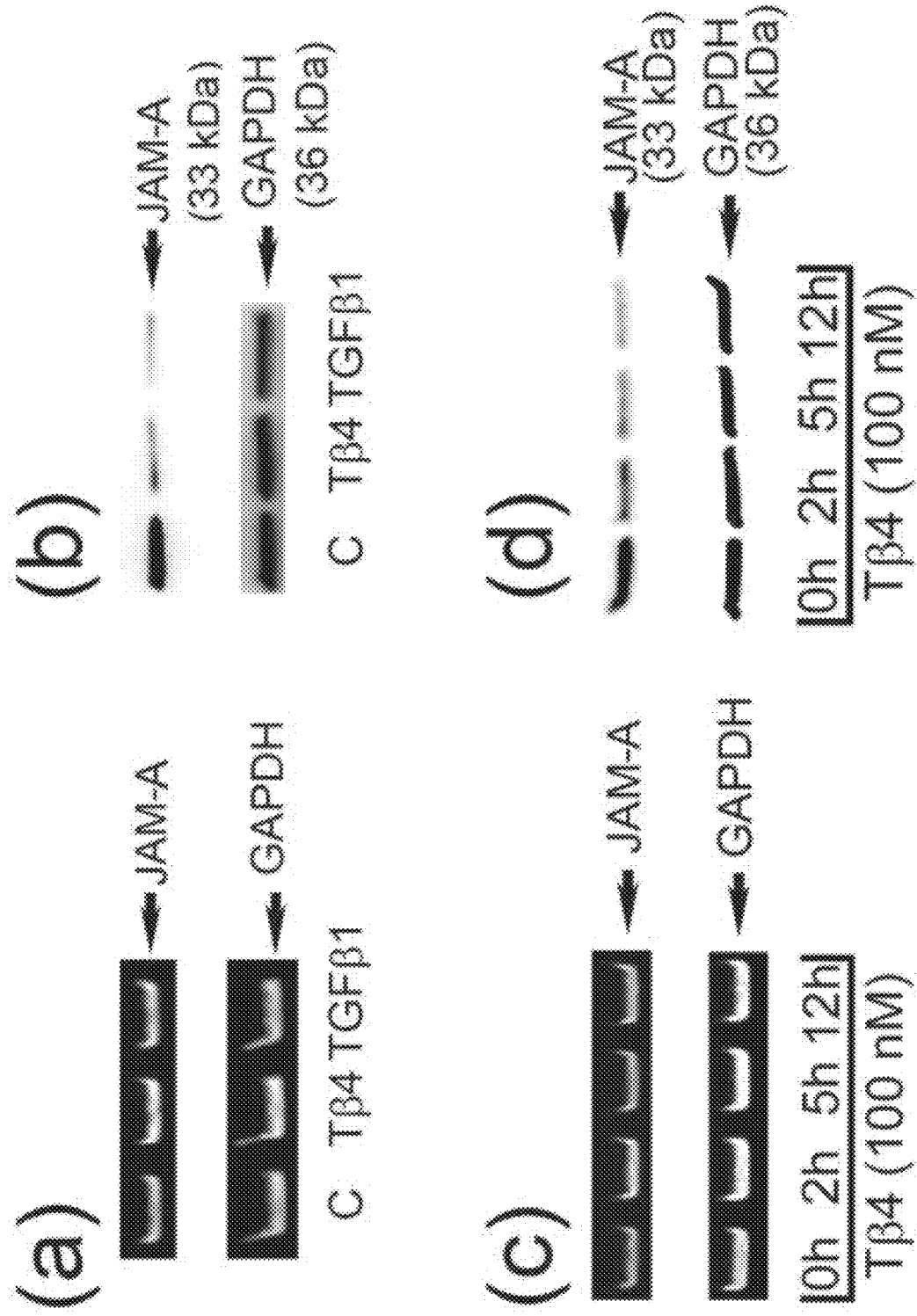
FIGS. 3a-3d are photographs of assays, the upper panels: RT-PCR (a) and Western blot (b) assay for detection of JAM-A expression levels using the RNA and protein extracts from HMEC-1 cells non-treated (C; control cells) or treated for 24 hours with Tβ4 at a concentration of 200 nM or with TGF-β1 at a concentration of 10 ng/ml. Lower panels: RT-PCR (c) and Western blot (d) assay for detection of JAM-A expression levels using the RNA and protein extracts from HMEC-1 cells incubated with Tβ4 at a concentration of 200 nM for 0, 2, 5, or 12 hours. The figures present the representative results of 3 independent experiments.

Moreover, exogenously added Tβ4 at 200 nM and TGF-β1 at 10 ng/mL evidently reduced the level of JAM-A protein in human microvascular endothelial cell line HMEC-1 after 24-hours incubation (FIG. 3b). The observed action of Tβ4 on JAM-A expression was time-dependent (FIG. 3d; incubation times: 0, 2, 5, or 12 hours; Tβ4 added at a concentration of 200 nM) and was similar to that one as for TGF-β1 that was used as the positive control for the reduction of JAM-A expression (FIG. 3b). However, there were no observed changes of JAM-A expression on mRNA level (FIGS. 3a and 3c).

Expression of JAM-A on the surface of HMEC-1 endothelial cell line was demonstrated by flow cytometry (FIGS. 4a-4d). JAM-A antigen, designated as CD321, was shown to be evidently present on HMEC-1 cells (black line on histogram vs. HMEC-1 cells labeled with isotype control antibody shown as the purple line). Exogenously added Tβ4 at 200 nM (red line on histogram) and TGF-β1 at 10 ng/ml (green line on histogram) slightly decreased JAM-A level on the membrane of HMEC-1 cells, whereas proinflammatory cytokine TNF-α at 10 ng/mL triggered a minor increase of CD321 expression on the surface of the tested endothelial cell line (blue line on histogram).

F11R Derived Peptide 4D (P4D) Blocks the Extravasation of Breast Cancer Cells

Soluble JAM-A inhibits the platelet aggregation and adhesion to the inflamed endothelium. Consequently, the decrease of sJAM-A plasma level produced by Tβ4/TGF-β1 could result in the promotion of breast cancer cell extravasation. Thus, the functional analysis of the breast cancer cells and endothelial cells from its environment was performed at the presence of the P4D peptide that blocks trans-homodimerization of JAM-A molecules. As shown in FIG. 5a, MECs adhered directly to the endothelium and adhesion of breast cancer cells was evidently upregulated by cytokines. TNF-α and IFN-γ only slightly induced the adhesion of non-tumorigenic MCF-10A cells to endothelium. Concurrently, P4D restrained the adhesion of MECs to the inflamed endothelial monolayer and this effect was the most pronounced for MDA-MB-231 cells (FIG. 5a). Likewise, transmigration of breast cancer cells across the endothelial monolayer activated with the same cytokines as well as with Tβ4 was hindered by P4D peptide (FIG. 5b and FIG. 7). Similar observations were performed in the case of non-tumorigenic MECs MCF-10A. Both mentioned above interactions of this cell line with cytokine-treated endothelium were markedly inhibited by P4D peptide (FIGS. 5a-5b, upper plots). Moreover, Tβ4 significantly elevated the TEM of MCF-10A cells in the presence of the Scr peptide (FIG. 5b). Transmigration of breast cancer cell lines MCF-7 and MDA-MB-231 across HMEC-1 monolayer was also slightly stimulated by Tβ4, but the differences were not statistically significant as compared with the CTRL (non-treated) cells (P=−0.6 for MCF-7 and P=0.3 for MDA-MB-231). P4D abrogated the Tβ4-activated TEM in the case of all tested MECs (FIG. 5b). The mutual effect of P4D and Tβ4 was not evaluated on the adhesion of breast cancer cells to endothelium, since Tβ4 is a potent activator of cellular motility. Similarly, the evident stimulation of TME by Tβ4 was observed, but it was significantly abrogated by P4D (FIG. 5b).

Peptide 4D Displays the Barrier-Protecting Effect on Endothelial Monolayer

Analysis of endothelial monolayer permeability by the macromolecular tracer assay revealed that transendothelial flux of 40-kDa FITC-dextran was elevated entirely when P4D was applied immediately after the cells were seeded (FIG. 6a). It is likely that P4D peptide prevented the de novo formation of TJs while it did not disrupt the preexisting ones.

Figure 6D:
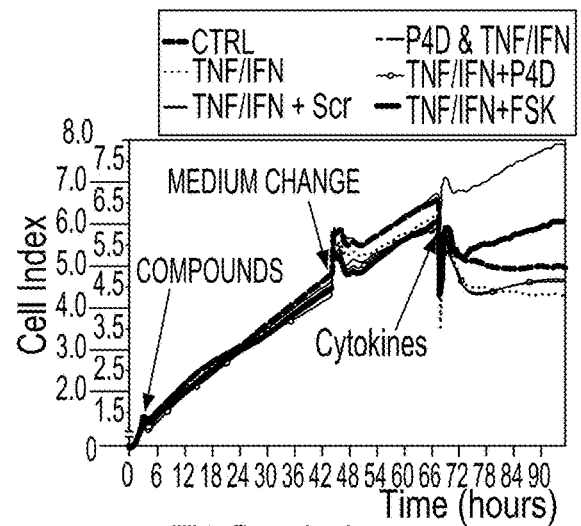
Figure 6E:
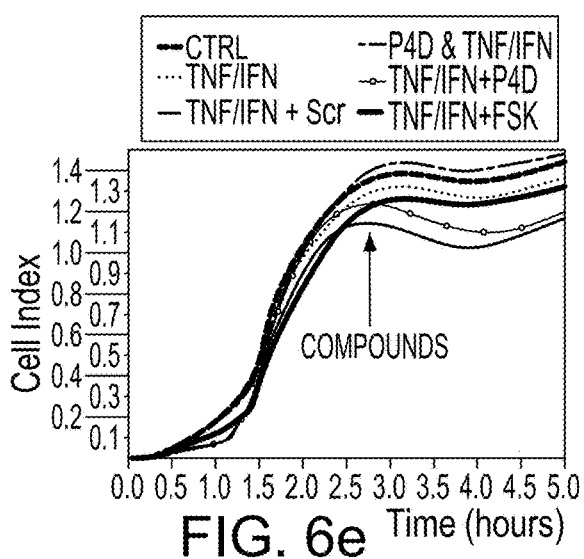
Figure 6F:
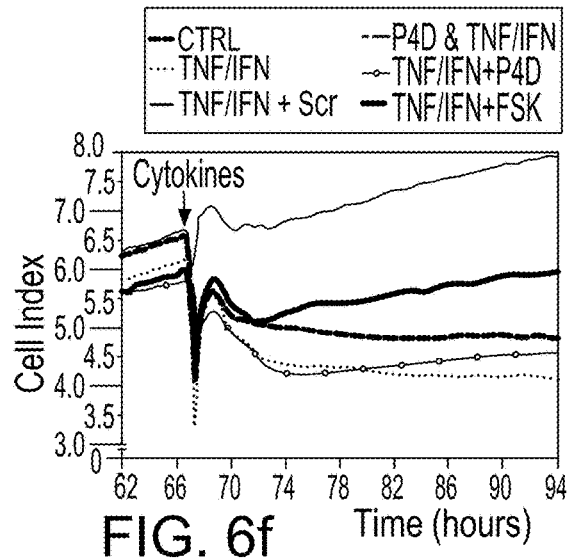

As detected by real time impedance-based analysis of HMEC-1 monolayer performed with the ACEA xCELLigence® system, P4D slightly strengthened endothelial barrier function as compared to controls when applied to the cells ~24 hours after the seeding, but this effect was apparently weaker than that one of forskolin (FSK) that was used here as the barrier promoting agent (FIG. 6b). Moreover, P4D did not reproduce the barrier-protecting effect of FSK when applied 24 hours after the cells were treated with the inflammatory cytokines (FIG. 6c). Therefore, an alternative experimental approach, where HMEC-1 monolayer was treated with the compounds (P4D, Scr, FSK) about 2.5 hours after plating, was implemented. At this time point the cells adhered to the bottom of the wells while they did not form a confluent monolayer as demonstrated by the low CI levels (FIGS. 6d and 6e). At this phase the tight junctions were not fully developed and only a minor fraction of JAM-A molecules formed trans-homophilic interactions. The endothelial monolayer was subjected to the treatment with inflammatory cytokines about 60 hours later, during the logarithmic growth phase (FIGS. 6d and 6f). One of the samples was designated as 'P4D & TNF/IFN'. In this case the cells were re-treated with P4D peptide concurrently with TNF/IFN treatment. As evidenced in FIG. 6d and with more details in FIG. 6f, the barrier-protecting effect of P4D was even more evident than that one of FSK, when P4D pre-treatment was followed by the second supplementary dose, applied simultaneously with the cytokines. On the other hand, P4D did not reveal any barrier-protecting properties when the supplementary dose was not applied (FIG. 6f).

Example 3

Peptide 4, as well as its D-amino acid analog (P4D), have been demonstrated to provide the basis for the drug development in the treatment of several cardiovascular disorders, including thrombosis, atherosclerosis, heart attacks and stroke, as disclosed in U.S. Pat. No. 9,556,235, which is incorporated by reference.

Further, several tumor inducers, namely Tβ4 (a potent activator of cancer cells migration and metastasis) and TGF-β1 (a major contributor of EMT) decrease the plasma levels of sJAM-A in the murine 4T1 breast cancer model. Soluble JAM-A has been shown to arrest the platelets aggregation and adhesion to the inflamed endothelium. Moreover, sJAM-A attenuated the transmigration of neutrophils across the endothelial monolayer. Thus, the present experiments demonstrated that P4D is able to restore the inhibitory action of sJAM-A. Accordingly, P4D peptide abrogates de novo formation of TJ as demonstrated by the inhibition of breast cancer cells adhesion to inflamed endothelium as well as by the suppression of breast cancer cells migration across the endothelial monolayer activated by inflammatory cytokines or by cellular motility inducers as Tβ4. Simultaneously, the JAM-A blocking peptide did not break up the preexisting junctions, thus endothelial monolayer was not deteriorated.

Many abbreviations have been used in the present specification, the following list provides their meanings if they are not previously provided:
ADAM: A disintegrin and metalloproteinase;
BCA: Bicinchoninic acid;
CAM: Cell adhesion molecule;
COSMIC: Catalogue of Somatic Mutations in Cancer;
CTRL: Control;
ELISA: Enzyme-linked immunosorbent assay;
EMT: Epithelial to mesenchymal transition;
FBS: Fetal bovine serum;
FITC: Fluorescein isothiocyanate;
FSK: Forskolin;
GAPDH: Glyceraldehyde 3-phosphate dehydrogenase;
HRP: Horseradish peroxidase;
IFN-γ: Interferon-γ;
JAM-A: Junctional adhesion molecule-A;
K2-EDTA: Dipotassium ethylenediaminetetraacetic acid;
MEC: Mammary epithelial cell;
NFκB: nuclear factor κ-light-chain-enhancer of activated B cells;
P4D: F11R-blocking peptide 4D;
PBS: Phosphate-buffered saline;
PDZ-GEF2: PDZ-guanine nucleotide exchange factor-2;
PVDF: Polyvinylidene difluoride;
qRT-PCR: Quantitative reverse transcription-polymerase chain reaction;
RTCA: Real-Time Cell Analysis;
Scr: Peptide 4D with the scrambled sequence;
SDS: Sodium dodecyl sulphate;
sJAM-A: Soluble JAM-A;
TBS: Tris-buffered saline;
Tβ4: Thymosin β4;
TEER: Transendothelial resistance;
TEM: Transendothelial migration,
TER: Transepithelial resistance;
TGF-β1: Transforming growth factor-β1;
TJ: Tight junction;
TMB: 3, 3, 5, 5'-tetramethylbenzidine;
TNF-α: Tumor necrosis factor-α.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A method of treating breast cancer, the method comprising administering to a subject diagnosed with breast cancer an effective amount of a cell adhesion molecule Receptor (F11R peptide).

2. The method of claim 1, wherein the F11R peptide is peptide 4D (P4D), wherein P4D is SEQ ID NO. 2.

3. The method of claim 1, where the effective amount of the F11R peptide is administered to the subject's inflamed endothelial layer.

4. The method of claim 1, further comprising administration of a chemotherapeutic.

* * * * *

SEQUENCE LISTING

<160> NUMBER OF SEQ ID NOS: 10

<210> SEQ ID NO 1
<211> LENGTH: 23
<212> TYPE: PRT
<213> ORGANISM: Homo sapiens

<400> SEQUENCE: 1

Ser Val Thr Val His Ser Ser Glu Pro Glu Val Arg Ile Pro Glu Asn
1               5                   10                  15

Asn Pro Val Lys Leu Ser Cys
            20

<210> SEQ ID NO 2
<211> LENGTH: 11
<212> TYPE: PRT
<213> ORGANISM: Homo sapiens

<400> SEQUENCE: 2

Ser Val Thr Glu Asp Thr Gly Thr Tyr Thr Cys
1               5                   10

<210> SEQ ID NO 3
<211> LENGTH: 11
<212> TYPE: PRT
<213> ORGANISM: Homo sapiens

<400> SEQUENCE: 3

Ser Thr Val Glu Thr Asp Thr Gly Thr Tyr Cys
1               5                   10

<210> SEQ ID NO 4
<211> LENGTH: 13
<212> TYPE: PRT
<213> ORGANISM: Homo sapiens

<400> SEQUENCE: 4

Lys Ser Val Thr Arg Glu Asp Thr Gly Thr Tyr Thr Cys
1               5                   10

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
cgagaggaaa ctgttgtgcc                                         20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
aacgagtctg gtggtgtctc                                         20

<210> SEQ ID NO 7
<211> LENGTH: 20
<212> TYPE: DNA
<213> ORGANISM: Artificial Sequence
<220> FEATURE:

```
<223> OTHER INFORMATION: forward primer

<400> SEQUENCE: 7
cttttcctcc gcaaccatgt                                                    20

<210> SEQ ID NO 8
<211> LENGTH: 20
<212> TYPE: DNA
<213> ORGANISM: Artificial Sequence
<220> FEATURE:
<223> OTHER INFORMATION: reverse primer

<400> SEQUENCE: 8
aggggcagca cagtcattta                                                    20

<210> SEQ ID NO 9
<211> LENGTH: 22
<212> TYPE: DNA
<213> ORGANISM: Artificial Sequence
<220> FEATURE:
<223> OTHER INFORMATION: forward primer

<400> SEQUENCE: 9
gagagatgat gaccttttg gc                                                  22

<210> SEQ ID NO 10
<211> LENGTH: 23
<212> TYPE: DNA
<213> ORGANISM: Artificial Sequence
<220> FEATURE:
<223> OTHER INFORMATION: reverse primer

<400> SEQUENCE: 10
ccatcaccat cttcccagga gcg                                                23
```